United States Patent [19]

Lüthy et al.

[11] Patent Number: 5,332,717

[45] Date of Patent: Jul. 26, 1994

[54] HETEROCYCLIC COMPOUNDS

[75] Inventors: Christoph Lüthy, Schwerzenbach; Jean-Pierre Obrecht, Zurich, both of Switzerland

[73] Assignee: Ciba-Geigy Corporation, Ardsley, N.Y.

[21] Appl. No.: 47,888

[22] Filed: Apr. 15, 1993

Related U.S. Application Data

[63] Continuation of Ser. No. 689,059, filed as PCT/CH90/00222, Sep. 19, 1990, abandoned.

[30] Foreign Application Priority Data

Oct. 12, 1989 [CH] Switzerland ............... 3716/89-5

[51] Int. Cl.$^5$ ............... C07D 409/12; C07D 407/12; A01N 43/54
[52] U.S. Cl. ............... 504/242; 504/243; 504/196; 544/300; 544/310; 544/316; 544/317; 544/318; 544/243
[58] Field of Search ............... 504/242, 243, 196; 544/300, 316

[56] References Cited

U.S. PATENT DOCUMENTS

| | | | |
|---|---|---|---|
| 4,770,691 | 9/1988 | Nezu et al. | 71/92 |
| 5,118,339 | 6/1992 | Tamaru et al. | 71/92 |

FOREIGN PATENT DOCUMENTS

| | | |
|---|---|---|
| 0001187 | 9/1978 | European Pat. Off. |
| 0223406 | 10/1986 | European Pat. Off. |
| 0249708 | 4/1987 | European Pat. Off. |
| 0287072 | 4/1988 | European Pat. Off. |
| 0287079 | 4/1988 | European Pat. Off. |
| 0315889 | 11/1988 | European Pat. Off. |
| 0336494 | 3/1989 | European Pat. Off. |

*Primary Examiner*—John M. Ford
*Attorney, Agent, or Firm*—George R. Dohmann

[57] ABSTRACT

The invention relates to compounds of formula

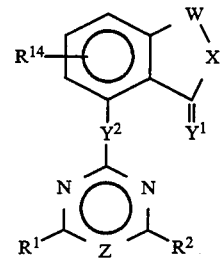

I wherein W, X, $Y^1$, $Y^2$, Z, $R^1$, $R^2$ and $R^{14}$ are as defined in the description, and to the preparation thereof, to weed control compositions and plant-growth-regulating compositions comprising such compounds as active ingredients, and to the use of the active ingredients or compositions for controlling weeds and for regulating plant growth.

21 Claims, No Drawings

HETEROCYCLIC COMPOUNDS

This application is a continuation of application Ser. No. 07/689,059, filed as PCT/CH90/00222, Sep. 19, 1990, now abandoned.

The present invention relates to heterocyclic compounds, namely 2-heterocyclyloxy/thio-pyrimidines and -1,3,5-triazines of the general formula

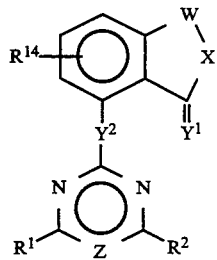

wherein
W is one of the divalent groups a)–d)

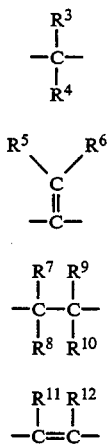

X, $Y^1$ and $Y^2$ are each oxygen or sulfur,
Z is $CR^{13}$ or nitrogen,
$R^1$ is hydrogen, fluorine, chlorine, $C_{1-3}$alkyl, halomethyl, methoxymethyl, $C_{1-3}$alkoxy, difluoromethoxy or methylthio,
$R^2$ is methyl, $C_{1-2}$alkoxy, $C_{1-2}$fluoroalkoxy, $C_{1-2}$alkylamino di($C_{1-2}$alkyl)amino or N-methoxymethylamino,
$R^3$ is hydrogen, fluorine, chlorine, bromine, unsubstituted or substituted $C_{1-6}$alkyl, $C_{2-3}$alkenyl, $C_{2-3}$alkynyl, unsubstituted or substituted phenyl, hydroxy, unsubstituted or substituted $C_{1-6}$alkoxy, $C_{1-6}$alkylthio, phenoxy, phenylthio, cyano, thiocyano, formyl, carboxy, $C_{2-5}$alkoxycarbonyl, carbamoyl, formyloxy, $C_{2-5}$alkanoyloxy, $C_{2-5}$alkoxycarbonyloxy, $C_{2-3}$alkylcarbamoyloxy, di($C_{1-2}$alkyl)carbamoyloxy or di($C_{1-2}$alkoxy)phosphonyl,
$R^4$ is hydrogen, $C_{1-6}$alkyl or trifluoromethyl,
$R^5$ is hydrogen, $C_{1-6}$alkyl or unsubstituted or substituted phenyl,
$R^6$ is hydrogen or methyl,
$R^7$, $R^8$ and $R^9$ each independently of the others is hydrogen or $C_{1-3}$alkyl,
$R^{10}$ is hydrogen or $C_{1-3}$alkoxy,
$R^{11}$ and $R^{12}$ each independently of the other is hydrogen or $C_{1-3}$alkyl,
$R^{13}$ is hydrogen, fluorine, chlorine or methyl and
$R^{14}$ is hydrogen, halogen, $C_{1-2}$alkyl or $C_{1-2}$alkoxy.

The compounds according to the invention, that is to say the compounds of formula I, have herbicidal activity and are suitable as active ingredients of weed control compositions. The compounds according to the invention furthermore have plant-growth-regulating activity; they are therefore suitable inter alia as compositions for positively influencing the growth of useful plants. The invention accordingly includes also weed control compositions and plant-growth-regulating compositions that comprise compounds according to the invention as active ingredients, to a process for the preparation of those compounds and to the use of the compounds and compositions for controlling weeds and for regulating plant growth.

In formula I above, "halogen" on its own or as part of a more complex group includes, for example, halomethyl, fluorine, chlorine, bromine and iodine, fluorine and chlorine generally being preferred. The alkyl, alkenyl and alkynyl radicals may be straight-chain or branched, as may also be the or each alkyl moiety of the alkoxy, alkylthio, alkoxycarbonyl groups and other groups containing alkyl. The preferred $C_{2-3}$alkenyl and -alkynyl groups are vinyl and ethynyl, respectively. A halomethyl or fluoroalkoxy group may have one or more fluorine atoms, examples of such groups being chloromethyl, trifluoromethyl and difluoromethoxy. Unsubstituted or substituted $C_{1-6}$ alkyl ($R^3$) is especially an alkyl group that may be substituted by halogen (especially chlorine), hydroxy, methoxy, ethoxy, nitro, cyano, vinyl, ethynyl, carboxy, $C_{2-5}$alkoxycarbonyl (especially methoxycarbonyl or ethoxycarbonyl) or by an unsubstituted or substituted (especially methoxy-substituted) phenyl group. The preferred unsubstituted or substituted alkyl group is unsubstituted or substituted methyl or ethyl, especially the former group. Unsubstituted or substituted $C_{1-6}$alkoxy ($R^3$) is especially an alkoxy group that may be substituted by halogen (especially fluorine or chlorine), vinyl, ethynyl, cyclopropyl, phenyl, $C_{1-2}$alkoxy, $C_{1-2}$alkylthio, cyano, carboxy, $C_{2-5}$alkoxycarbonyl (especially methoxycarbonyl or ethoxycarbonyl), carbamoyl, N-($C_{1-2}$alkyl)carbamoyl, N,N-di($C_{1-2}$alkyl)carbamoyl or by $C_{3-5}$alkylideneiminooxy. A substituted phenyl group ($R^3$, $R^5$) may contain as substituents especially fluorine, chlorine, methyl, methoxy or trifluoromethyl. The preferred $C_{2-5}$alkanoyloxy, $C_{2-5}$alkoxycarbonyloxy, $C_{2-3}$alkylcarbamoyloxy, di($C_{1-2}$alkyl)carbamoyloxy and di($C_{1-2}$alkoxy)phosphonyl groups ($R^3$) are acetyloxy or propionyloxy; methoxycarbonyloxy or ethoxycarbonyloxy; methylcarbamoyloxy; dimethylcarbamoyloxy; and dimethoxyphosphonyl, respectively.

Owing to the possible presence of an asymmetric carbon atom in the compounds of formula I, the compounds may occur in the form of optical isomers. Owing to the presence of a possible aliphatic C=C double bond, geometrical isomers also may occur. Formula I is intended to include these and possible further isomeric forms and mixtures thereof.

A special group of compounds of formula I consists of those compounds I wherein W is a group a) wherein $R^3$ is hydrogen, fluorine, chlorine, bromine, unsubstituted or substituted $C_{1-6}$alkyl (wherein a substituent which may possibly be present is especially halogen, methoxy, ethoxy, nitro, cyano, methoxycarbonyl, ethoxycarbonyl, phenyl or methoxyphenyl), $C_{2-3}$alkenyl, $C_{2-3}$alkynyl, unsubstituted or substituted phenyl (wherein a substituent which may possibly be present is especially fluorine, chlorine, methyl, methoxy or trifluoromethyl), hydroxy, $C_{1-6}$alkoxy, $C_{1-6}$alkylthio, phenoxy, phenylthio, cyano or $C_{2-5}$alkoxycarbonyl and $R^4$ is hydrogen or $C_{1-6}$alkyl, or $R^3$ is hydrogen, fluorine, chlorine, bromine, $C_{1-6}$alkyl, hydroxy, $C_{1-6}$alkoxy, $C_{1-6}$alkylthio, phenoxy, phenylthio or cyano and $R^4$ is trifluoromethyl; or W is a group b), c) or d) wherein $R^5$ to $R^{12}$ are as defined above; and X is oxygen, $Y^1$ and $Y^2$ are each oxygen or sulfur Z is $CR^{13}$ or nitrogen, $R^1$ is fluorine, chlorine, $C_{1-3}$alkyl, fluoromethyl, methoxymethyl, $C_{1-3}$alkoxy, difluoromethoxy or methylthio, $R^2$ is methyl, $C_{1-2}$alkoxy or $C_{1-2}$fluoroalkoxy, $R^{13}$ is hydrogen, fluorine, chlorine or methyl, and $R^{14}$ is hydrogen.

Independently of one another, W is preferably a group a) or b), especially a group a); X and/or $Y^1$, especially, however both X and $Y^1$ is/are preferably oxygen; $Y^2$ is preferably oxygen, Z is preferably CH or nitrogen, especially CH; $R^1$ is preferably hydrogen, chlorine, methyl, methoxy or difluoromethoxy and $R^2$ is preferably methoxy, ethoxy, methylamino, dimethylamino or N-methoxymethylamino, the combination of $R^1$ and $R^2$ wherein at least one methoxy group is present being especially preferred; $R^3$ of the group a) is preferably hydrogen, vinyl, ethynyl, hydroxy, $C_{1-4}$alkoxy, $C_{1-2}$alkoxy that is substituted by halogen, vinyl, ethynyl, $C_{1-2}$alkoxy, cyano, carboxy or by $C_{2-3}$alkoxycarbonyl, $C_{1-2}$alkylthio, cyano, carboxymethyl, $C_{2-3}$alkoxycarbonylmethyl or carbamoyl and $R^4$ is preferably hydrogen or $C_{1-4}$alkyl; $R^5$ of the group b) is preferably hydrogen or $C_{1-3}$alkyl and $R^6$ is preferably hydrogen; $R^7$, $R^8$ and $R^9$ of the group c) are preferably each hydrogen or methyl; $R^{11}$ and $R^{12}$ of the group d) are preferably each hydrogen or methyl; and $R^{14}$ is preferably hydrogen or methyl, especially hydrogen.

Especially preferred individual compounds of formula I are:

7-[(4,6-dimethoxy-pyrimidin-2-yl)oxy]-3-methyl-phthalide,
7-[(4,6-dimethoxy-pyrimidin-2-yl)oxy]-phthalide,
3-ethyl-7-[(4,6-dimethoxy-pyrimidin-2-yl)oxy]-phthalide,
7-[(4,6-dimethoxy-pyrimidin-2-yl)oxy]-3-isopropyl-phthalide,
7-[(4,6-dimethoxy-pyrimidin-2-yl)oxy]-3-methoxy-phthalide,
7-[(4-methoxy-6-methyl-pyrimidin-2-yl)oxy]-3-methylphthalide,
7-[(4,6-dimethoxy-1,3,5-triazin-2-yl)oxy]-3-methyl-phthalide,
3-ethylidene-7-[(4,6-dimethoxy-pyrimidin-2-yl)oxy]-phthalide (especially the (Z) isomer thereof),
8-[(4,6-dimethoxy-pyrimidin-2-yl)oxy]-3-methyl-isochroman-1-one,
7-[(4,6-dimethoxy-pyrimidin-2-yl)thio]-3-methyl-phthalide,
3-ethoxy-7-[(4,6-dimethoxy-pyrimidin-2-yl)oxy]-phthalide,
7-[(4,6-dimethoxy-pyrimidin-2-yl)oxy]-3,6-dimethyl-phthalide,
7-[(4,6-dimethoxy-pyrimidin-2-yl)oxy]-3-methoxy-3-methyl-phthalide,
3-carbamoyl-7-[(4,6-dimethoxy-pyrimidin-2-yl)oxy]-phthalide,
3-(2-chloroethoxy)-7-[(4,6-dimethoxy-pyrimidin-2-yl)oxy]-phthalide,
7-[(4,6-dimethoxy-pyrimidin-2-yl)oxy]-3-propargyloxy-phthalide,
7-[(4,6-dimethoxy-pyrimidin-2-yl)oxy]-3-(n-propoxy)-phthalide,
7-[(4,6-dimethoxy-pyrimidin-2-yl)oxy]-3-(2-methoxyethoxy)-phthalide,
7-[(4-chloro-6-methoxy-pyrimidin-2-yl)oxy]-3-methyl-phthalide,
7-[(4-methoxy-pyrimidin-2-yl)oxy]-3-methyl-phthalide,
7-[(4-ethoxy-6-methoxy-pyrimidin-2-yl)oxy]-3-methyl-phthalide,
7-[(4-chloro-6-methoxy-pyrimidin-2-yl)oxy]-3-methoxy-phthalide,
7-[(4,6-dimethoxy-1,3,5-triazin-2-yl)thio]-3-methyl-phthalide,
7-[(4-dimethylamino-6-methoxy-1,3,5-triazin-2-yl)oxy]-3-methyl-phthalide,
7-[(4-methoxy-6-methyl-1,3,5-triazin-2-yl)oxy]-3-methyl-phthalide,
7-[(4-methoxy-6-methylamino-1,3,5-triazin-2-yl)oxy]-3-methyl-phthalide,
7-[(4-chloro-6-methylamino-1,3,5-triazin-2-yl)oxy]-3-methyl-phthalide,
3-ethyl-7-[(4,6-dimethoxy-1,3,5-triazin-2-yl)oxy]-phthalide,
8-[(4,6-dimethoxy-pyrimidin-2-yl)oxy]-3,4-dimethyl-isochroman-2-one,
7-[(4,6-dimethoxy-pyrimidin-2-yl)oxy]-3-hydroxy-phthalide,
7-[(4,6-dimethoxy-pyrimidin-2-yl)oxy]-3-methylthio-phthalide,
7-[(4,6-dimethoxy-pyrimidin-2-yl)oxy]-3-vinyl-phthalide,
3-cyano-7-[(4,6-dimethoxy-pyrimidin-2-yl)oxy]-phthalide,
3-cyanomethoxy-7-[(4,6-dimethoxy-pyrimidin-2-yl)oxy]-phthalide,
7-[(4,6-dimethoxy-pyrimidin-2-yl)oxy]-3-(methoxycarbonyl-methoxy)-phthalide,
3-ethoxycarbonylmethyl-7-[(4,6-dimethoxy-pyrimidin-2-yl)oxy]-phthalide,
7-[(4,6-dimethoxy-pyrimidin-2-yl)oxy]-3-methyl-2-benzothiophen-1(3H)-one,
7-[(4,6-dimethoxy-pyrimidin-2-yl)oxy]-3-methyl-isobenzofuran-1(3H)-thione,
7-[(4,6-dimethoxy-1,3,5-triazin-2-yl)oxy]-3-methyl-isobenzofuran-1(3H)-thione,
7-[(4-difluoromethoxy-6-methoxy-pyrimidinyl)oxy]-3-methyl-phthalide,
8-[(4,6-dimethoxy-pyrimidin-2-yl)oxy]-4-methylisochroman-1-one and
3-acetoxy-7-[(4,6-dimethoxy-pyrimidin-2-yl)oxy]-phthalide.

Further representatives of compounds of formula I are:
7-[(4,6-dimethoxy-pyrimidin-2-yl)oxy]-3-isobutyl-phthalide,
7-[(4,6-dimethoxy-pyrimidin-2-yl)oxy]-3-sec-butyl-phthalide,
those compounds of formula I wherein W is a group a), X, $Y^1$ and $Y^2$ are all oxygen, Z is CH, $R^1$ and $R^2$ are both methoxy, $R^4$ and $R^{14}$ are both hydrogen and $R^3$ is bromine, chloromethyl, trichloromethyl, hydroxymethyl, methoxymethyl, cyanomethyl, carboxymethyl, methoxycarbonylmethyl, allyl, ethynyl, propargyl, n-butoxy, cyclopropylmethoxy, difluoromethoxy, 2,2,2-trifluoroethoxy, methoxymethoxy, methylthiomethoxy, 2-methylthioethoxy, carboxymethoxy, 1-carboxyethoxy, 1-methoxycarbonylethoxy, ethoxycarbonylmethoxy, 1-ethoxycarbonylethoxy, N-methylcarbamoylmethoxy, 2-(N,N-dimethylamino)-ethoxy, formyl, carboxy, ethoxycarbonyl, formyloxy, acetyloxy, methoxycarbonyloxy, ethoxycarbonyloxy or N,N-dimethylcarbamoyloxy;

those compounds of formula I wherein W is a group a), X, $Y^1$ and $Y^2$ are all oxygen, Z is CH, $R^1$ and $R^2$ are both methoxy $R^4$ is methyl, $R^{14}$ is hydrogen and $R^3$ is fluorine vinyl, hydroxy, ethoxy, methylthio, carboxy or methoxycarbonyl;

3-ethyl-7-[(4,6-dimethyl-pyrimidin-2-yl)oxy]-3-methoxyphthalide,

7-[(4,6-dimethyl-pyrimidin-2-yl)oxy]-3-methoxy-3-trifluoromethyl-phthalide, 3-ethoxy-7-[(4,6-dimethoxy-pyrimidin-2-yl)oxy]-3-trifluoromethyl-phthalide, those compounds of formula I wherein W is a group a), X, $Y^1$ and $Y^2$ are all oxygen, Z is CH, $R^1$ and $R^2$ are both methoxy, $R^3$ is methyl, $R^4$ is hydrogen and $R^{14}$ is 4-fluoro, 5-fluoro, 6-fluoro, 6-chloro, 4-methyl, 5-methyl, 4-methoxy, 5-methoxy or 6-methoxy;

those compounds of formula I wherein W is a group a), X, $Y^1$ and $Y^2$ are all oxygen, Z is CH, $R^2$ is methoxy, $R^3$ is methyl, $R^4$ and $R^{14}$ are both hydrogen and $R^1$ is fluorine, ethyl or methylthio;

those compounds of formula I wherein W is a group a), X, $Y^1$ and $Y^2$ are all oxygen, Z is CH, $R^1$ is methoxy, $R^3$ is methyl, $R^4$ and $R^{14}$ are both hydrogen and $R^2$ is methylamino, dimethylamino or ethylamino;

those compounds of formula I wherein W is a group a), X, $Y^1$ and $Y^2$ are all oxygen, Z is nitrogen, $R^1$ and $R^2$ are both methoxy, $R^4$ and $R^{14}$ are both hydrogen and $R^3$ is hydrogen, ethyl, n-propyl or n-butyl;

7-[(4-methoxy-6-{N-methoxymethylamino}-1,3,5-triazin-2-yl)oxy]-3-methyl-phthalide, 7-[(4,6-dimethoxy-1,3,5-triazin-2-yl )oxy]-3-methoxy-3-methyl-phthalide, 7-[(4,6-dimethyl-1,3,5-triazin-2-yl )oxy]-3-methyl-phthalide.

those compounds of formula I wherein W is a group a), X, $Y^1$ and $Y^2$ are all oxygen, Z is CH, $R^1$ and $R^2$ are both difluoromethoxy, $R^3$ is hydrogen, methoxy or ethoxy, $R^4$ is hydrogen, methyl or ethyl and $R^{14}$ is hydrogen;

those compounds of formula I wherein W is a group a), X and $Y^1$ are both oxygen, $Y^2$ is sulfur, Z is CH, $R^1$ and $R^2$ are both methoxy, $R^4$ and $R^{14}$ are both hydrogen, and $R^3$ is hydrogen, ethyl, methoxycarbonylmethyl, hydroxy, methoxy, ethoxy or methoxycarbonyloxy;

7-[(4,6-dimethoxy-pyrimidin-2-yl)thio]-3-methyl-isobenzofuran-1(3H)-thione,

7-[(4,6-dimethoxy-pyrimidin-2-yl)thio]-3-methyl-2-benzothiophen-1(3H)-one,

7-[(4,6-dimethoxy-pyrimidin-2-yl)oxy]-3-methyl-2-benzothiophen-1(3H)-thione, 3-ethyl-7-[(4,6-dimethoxy-pyrimidin-2-yl)oxy]-isobenzofuran-1(3H)-thione, 7-[(4,6-dimethoxy-pyrimidin-2-yl)oxy]-3-methoxy-isobenzofuran-1(3H)-thione, 3-ethyl-7-[(4,6-dimethoxy-pyrimidin-2-yl)oxy]-2-benzothiophen-1(3H)-one, 7-[(4,6-dimethoxy-pyrimidin-2-yl)oxy]-3-methoxy-2-benzothiophen-1(3H)-one, 7-[(4,6-dimethyl-pyrimidin-2-yl)thio]-3-methyl-phthalide, 7-[(4-methoxy-6-methyl-pyrimidin-2-yl)thio]-3-methyl-phthalide, 7-[(5-chloro-4,6-dimethoxy-pyrimidin-2-yl)thio]-3-methyl-phthalide, 7-[(4,6-dimethoxy-5-fluoro-pyrimidin-2-yl)oxy]-3-methyl-phthalide, 7-[(4,6-dimethoxy-5-methyl-pyrimidin-2-yl)oxy]-3-methyl-phthalide, 7-[(5-chloro-4,6-dimethoxy-pyrimidin-2-yl)oxy]-3-methyl-phthalide, 7-[(4,6-dimethoxy-pyrimidin-2-yl)oxy]-3-methylidene-phthalide, 7-[(4,6-dimethoxy-pyrimidin-2-yl)oxy]-3-propylidene-phthalide, 3-butylidene-7-[(4,6-dimethoxy-pyrimidin-2-yl)oxy]-phthalide, 3-ethylidene-7-[(4,6-dimethoxy-1,3,5-triazin-2-yl)oxy]-phthalide, 3-methylidene-7-[(4,6-dimethoxy-1,3,5-triazin-2-yl)oxy]-phthalide, those compounds of formula I wherein W is a group c), X, $Y^1$ and $Y^2$ are all oxygen, Z is CH, $R^1$ and $R^2$ are both methoxy, $R^7$, $R^8$ and $R^9$ are all hydrogen, $R^{14}$ is hydrogen and $R^{10}$ is hydrogen, methoxy or ethoxy;

8-[(4-methoxy-6-methyl-pyrimidin-2-yl)oxy]-4-methyl-isochroman-1-one,

8-[(4,6-dimethyl-pyrimidin-2-yl)thio]-3-methyl-isochroman-1-one,

8-[(4,6-dimethoxy-1,3,5-triazin-2-yl)oxy]-isochroman-1-one,

8-[(4,6-dimethoxy-1,3,5-triazin-2-yl)oxy]-4-methyl-isochroman-1-one,

8-[(4,6-dimethoxy-pyrimidin-2-yl)oxy]-4-methyl-isochromen-1-one, 4-ethyl-8-[(4,6-dimethoxy-pyrimidin-2-yl)oxy]-isochromen-1-one, 8-[(4,6-dimethoxy-pyrimidin-2-yl)oxy]-3,4-dimethyl-isochromen-1-one and 8-[(4,6-dimethoxy-1,3,5-triazin-2-yl)oxy]-3-methyl-isochromen-1-one.

The process according to the invention for the preparation of compounds of formula I comprises reacting a compound of the general formula

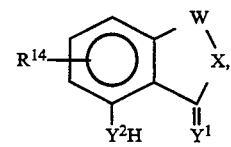

II wherein W, X, $Y^1$, $Y^2$ and $R^{14}$ are as defined above, with a compound of the general formula

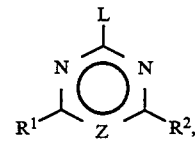

III wherein $R^1$ $R^2$ and Z are as defined above and L is a leaving group.

The expression "leaving group" (L) is to be understood as meaning especially a halogen atom, preferably chlorine or bromine, or an unsubstituted or substituted alkylthio, benzylthio, phenylthio, alkylsulfinyl, benzylsulfinyl, phenylsulfinyl, alkylsulfonyl, benzylsulfonyl, phenylsulfonyl, alkylsulfonyloxy, benzylsulfonyloxy, phenylsulfonyloxy or 3-alkylsulfonyl-1H-1,2,4-triazol- 1-yl group (e.g. 3-methylsulfonyl-1H-1,2,4-triazol-1-yl). Among such sulfur-containing leaving groups L, methanesulfonyl, ethanesulfonyl and benzylsulfonyl are especially preferred.

The reaction is advantageously carried out in an inert diluent, in the presence of a base or a reaction-accelerating additive, and at temperatures of from 0° C. to 160° C., preferably from 20° C. to 100° C. or the boiling point of the reaction mixture. Suitable diluents are especially organic solvents, preferably aprotic solvents, such as aliphatic or cyclic ethers, for example dimethoxyethane and tetrahydrofuran; aliphatic ketones, for example acetone and 2-butanone; aliphatic nitriles, for example acetonitrile and propionitrile; dimethylformamide; dimethylacetamide; and heteroaromatic compounds, for example pyridine and lutidine, and suitable bases are especially alkali metal hydrides, for example sodium hydride and potassium hydride; alkaline earth metal hydrides, for example calcium hydride; alkali metal hydrogen carbonates, for example sodium hydrogen carbonate and potassium hydrogen carbonate; alkali metal carbonates, for example sodium carbonate and potassium carbonate; alkaline earth metal carbonates, for example calcium carbonate and magnesium carbonate; aliphatic tertiary amines, for example triethylamine; fully substituted amidines, for example diazabicycloundecene; and basic heteroaromatic compounds, for example pyridine. Suitable reaction-accelerating additives are especially crown ethers and phase-transfer catalysts, but also substances that accelerate the reaction by temporarily replacing the leaving group L, for example in the case where L=halogen by activating the leaving group L. An example of the former substances is dimethylaminopyridine. Examples of the latter substances are silver and copper salts, such as silver nitrate and copper(I) chloride.

Further processes for the manufacture of those compounds of formula I according to the invention wherein W is a group a) or b) and X and $Y^1$ are each oxygen comprise subjecting a compound of the general formula

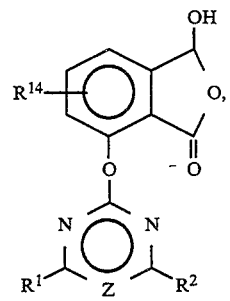

wherein $R^1$, $R^2$, $R^{14}$ and Z are as defined above, to a corresponding alkylation, acylation, carbonylation, carbamoylation, halogenation, substitution, Grignard or Wittig reaction, this being done analogously to the respective methods described hereinafter that are applied in connection with the preparation of the starting materials of formula II.

Those compounds of formula I wherein X and/or $Y^1$ are/is sulfur can also be prepared by sulfuration of the corresponding compounds I wherein X and/or $Y^1$ are-/is oxygen.

The resulting compounds of formula I can be isolated and purified by methods that are known per se.

If a controlled synthesis for the isolation of pure isomers is not carried out, the product may be obtained in the form of a mixture of two or more isomers. The isomers can be separated by methods that are known per se. If desired, for example, pure optically active isomers can also be prepared by synthesis from corresponding optically active starting materials.

Some of the starting materials of formula II are novel and some are known. For example, 7-hydroxyphthalide and 3,7-dihydroxy-phthalide (compounds of formula II wherein W is methylene and hydroxymethylene, respectively, X, $Y^1$ and $Y^2$ are each oxygen and $R^{14}$ is hydrogen) are known from E. L. Eliel et al., J. Org. Chem. 18, 1679 ff. (1953). The preparation of 7-hydroxy-3-methyl-phthalide and 3-ethyl-7-hydroxy-phthalide is furthermore described in S. Kushner et al., J.A.C.S. 75, 1097 ff. (1953) and J. Blair and G. T. Newbold, J. Org. Chem. 1955, 2871 ff., respectively. A method of obtaining 3,7-dihydroxy-3-methyl-phthalide is also known [see Z. Horii et al., J. Pharm. Soc. Japan 74, 466 ff. (1954)]. The novel starting materials of formula II can be prepared by methods that are known per se.

Those starting materials of formula II wherein W is a group a) or b) and X and $Y^1$ are both oxygen can be prepared in a manner known per se, for example according to the following Reaction Schemes 1 and 2:

Reaction Scheme 1

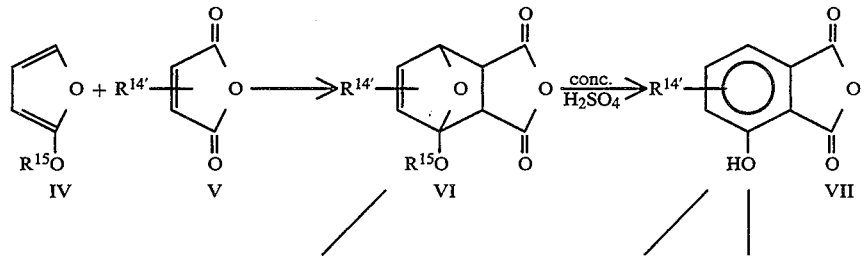

-continued
Reaction Scheme 1
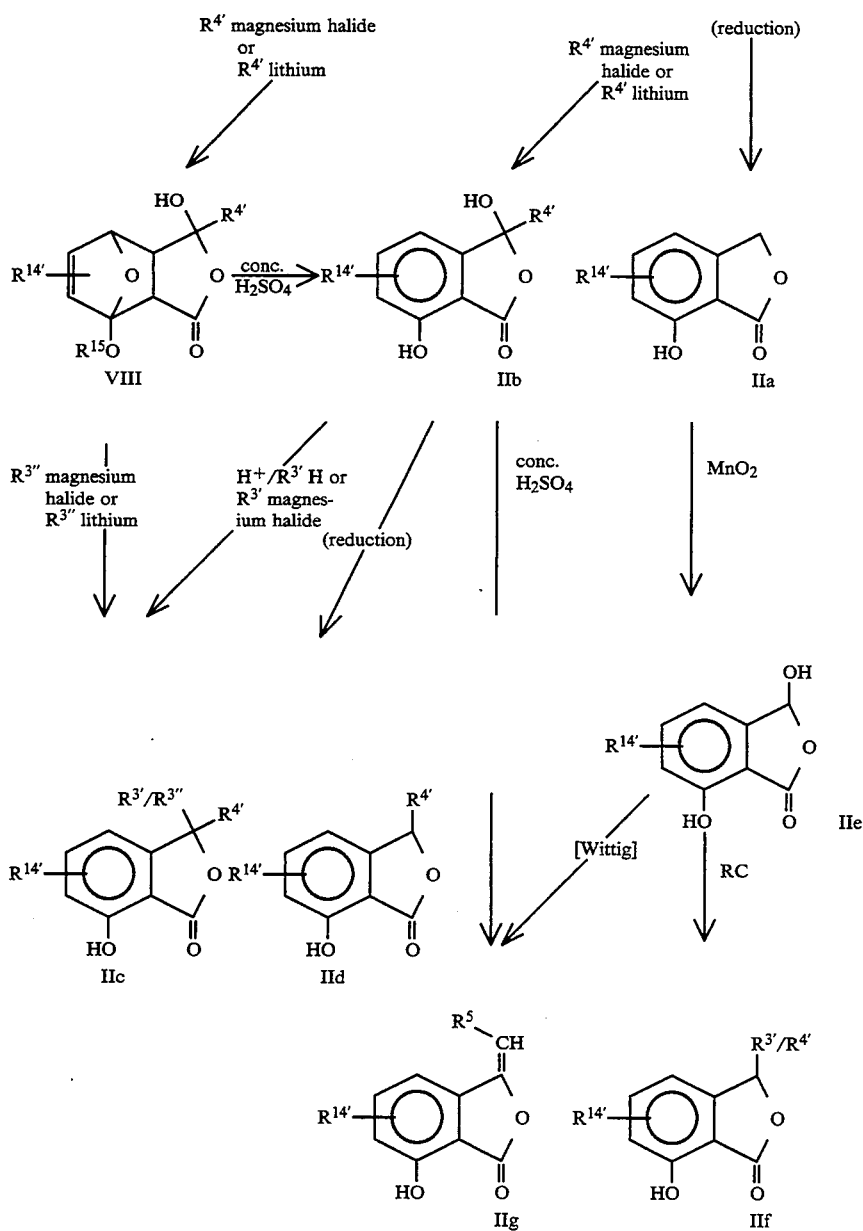
Reaction Scheme 2
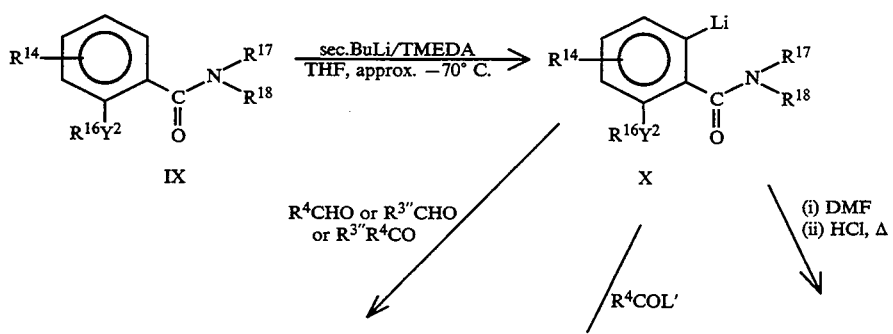

-continued
Reaction Scheme 2

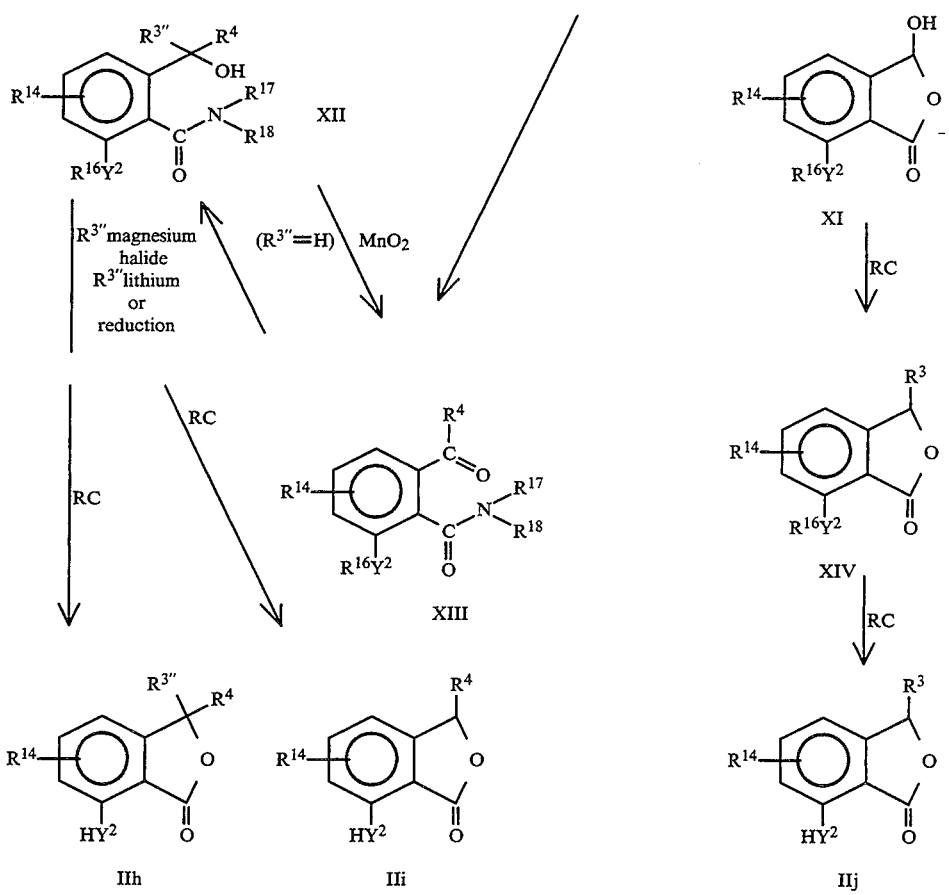

In the above Reaction Schemes 1 and 2, $Y^2$, $R^3$, $R^4$, $R^5$ and $R^{14}$ are as defined above; $R^{3'}$ is unsubstituted or substituted $C_{1-6}$alkyl, $C_{2-3}$alkenyl, $C_{2-3}$alkynyl, unsubstituted or substituted phenyl or unsubstituted or substituted $C_{1-6}$-alkoxy; $R^{3''}$ is unsubstituted or substituted $C_{1-6}$alkyl, $C_{2-3}$alkenyl, $C_{2-3}$alkynyl or unsubstituted or substituted phenyl; $R^{4'}$ is $C_{1-6}$alkyl; $R^{14'}$ is hydrogen or $C_{1-2}$alkyl; $R^{15}$ is alkanoyl, especially $C_{2-5}$alkanoyl, or a group —Si(CH$_3$)$_2$R$^{19}$ wherein $R^{19}$ is $C_{1-6}$alkyl; $R^{16}$ is hydrogen, methyl, tert-butyl or a protecting group customary in chemistry, such as, for example, benzyl, p-methoxybenzyl or methoxyethoxymethyl; $R^{17}$ is hydrogen or $C_{1-2}$alkyl and $R^{18}$ is $C_{1-4}$alkyl, or $R^{17}$ and $R^{18}$ together are tetramethylene that may be substituted by a methoxy or hydroxymethyl group.

The individual reactions, such as, for example, the various Grignard reactions using $R^{4'}$magnesium halide, $R^{4'}$lithium, $R^{3'}$magnesium halide, $R^{3''}$magnesium halide or $R^{3''}$lithium, the hydrolysis with concentrated sulfuric acid ("conc. H$_2$SO$_4$"), the reduction of a ring carbonyl group (for example in reaction step VII→IIa) or of a hydroxy group (for example in reaction step IIb→IId), the oxidation by means of manganese dioxide ("MnO$_2$") and the Wittig reaction, are familiar to one skilled in the art. For example, compounds of formula VII can be prepared from compounds of formula VI according to the instructions of J.-A. H. Näsman, Synthesis 1985, 788 (in this case $R^{15}$ is a 2,2-dimethylpropanoyloxy group). Compounds of formula VII can furthermore be prepared, for example, from the corresponding o-nitrophthalic acid anhydrides in accordance with generally known instructions—see, for example, E. L. Eliel, J.A.C.S. 77, 5092 ff. (1955). In that method, the nitro group is first reduced and the resulting compound is then converted into the corresponding hydroxy compound by diazotisation. Further relevant references in the literature with regard to suitable reaction conditions for certain reaction steps are J. Blair and G. T. Newbold, J. Org. Chem. 1955, 2871 ff. and B. L. Chenard et al., J. Org. Chem. 49, 318 ff. (1984).

In Reaction Scheme 2, TMEDA denotes tetramethylethylenediamine, THF denotes tetrahydrofuran, DMF denotes dimethylformamide and L' denotes a leaving group, such as chlorine, acetyl, imidazolyl, N,O-dimethylhydroxylamino or dimethylamino. The preferred groups NR$^{17}$R$^{18}$ for the direct metallation in the ortho-position with respect to the carboxamide function CONR$^{17}$R$^{18}$ (reaction step IX→X) are diethylamino [see V. Snieckus, Heterocycles 14, 1649 ff. (1980)], methylamino [see S. N. Yeola and R. S. Mali, Ind. J. Chem. 25B, 804 ff. (1986) and N. S. Narasimhan and R. S. Mali, Synthesis 1983, 957 ff.] and tert-butyl-methylamino [see D. B. Reitz and S. M. Massey, J. Org. Chem. 55, 1375 ff. (1990)].

In the few instances in which the reaction conditions (RC) are not specified, especially in process steps IIe→IIf and XI→XIV, the reaction conditions depend upon the nature of the group $R^3$ or $R^4$ to be introduced. If $R^3$ is unsubstituted or substituted $C_{1-6}$alkyl, $C_{2-3}$alkenyl, $C_{2-3}$alkynyl or unsubstituted or substituted phenyl ($R^{3''}$) or $R^4$ is $C_{1-6}$alkyl ($R^{4'}$), there is advantageously used as the reagent containing $R^{3''}$- or $R^{4'}$- the corresponding $R^{3''}$magnesium halide or $R^{4'}$magnesium halide, respectively, or $R^{3''}$lithium or $R^{4'}$lithium, respectively, whereas if $R^3$ is unsubstituted or substituted $C_{1-6}$alkoxy, the starting material IIb or IIe is treated with the corresponding hydroxy compound $R^3H$ advantageously with acid catalysis, for example using sulfuric acid, p-toluenesulfonic acid or trifluoroacetic acid. Examples of the former reaction type are described inter alia by J. Grandguillot and F. Roussac in Synthesis 1979, 607 ff., and by P. Canonne et al. in Tetrahedron Lett. 26, 4719 (1985).

With regard to reaction steps XII→IIh, XII→IIi and XIV→IIj, it is also generally known that a phenolic methyl ether group or the corresponding thioether group ($R^{16}$ is methyl) can readily be cleaved to the hydroxy or thio group ($R^{16}$ is hydrogen), respectively, with hydrogen bromide in water or glacial acetic acid, with boron tribromide or with the boron tribromide-dimethyl sulfide complex in methylene dichloride or ethylene dichloride. Other suitable cleavage reagents are aluminium trichloride, boron trichloride, dimethyl borobromide in methylene chloride, and alkylmercaptides, for example sodium ethylmercaptide in toluene or xylene.

Those starting materials of formula IIb wherein $R^{4'}$ is methyl or ethyl, and the corresponding protected compounds, can also be prepared by heating a corresponding phthalic acid anhydride with malonic acid or methylmalonic acid in the presence of a base, for example triethylamine (TEA) or pyridine (Py), which may additionally serve as diluent, until the evolution of carbon dioxide has ceased, this being carried out according to the following equation:

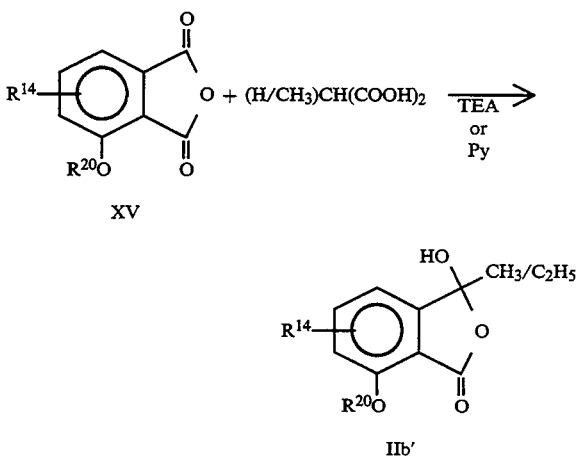

wherein $R^{20}$ is hydrogen or methyl.

Further methods for the preparation of the starting materials of formula II are known in addition from the expert literature. For example, the 3-hydroxyphthalides of formula XI indicated in Reaction Scheme 2 can also be prepared according to the teaching of B. M. Trost et al., J. Org. Chem. 45, 1835 ff. (1980), F. Hauser & R. Lee, J. Org. Chem. 45, 3061 ff. (1980), and J. N. Freskos et al., J. Org. Chem. 50, 805 ff. (1985), and these can then be converted into the corresponding starting materials of formula IIg or IIj as indicated above.

In order to obtain optically active compounds of formula IIi in the manner described above, a compound of formula IIb, IIb' or XIII can be reacted in the presence of an optically active reducing agent, such as, for example, the chiral lithium aluminium hydride reagent modified by binaphthol, (R)- or (S)-BINAL-H, [see R. Noyori et al., J.A.C.S. 106, 6717 ff. (1984)] or in the presence of an optically active, chiral hydrogenation catalyst, such as, for example, ruthenium [(R)- or (S)-BINAP] [see R. Noyori et al., J.A.C.S 109, 5856 ff., (1987)].

A further variant for the preparation of optically active compounds of formula IIi comprises treating a chiral carbinol in accordance with the method of Trost et al., J. Org. Chem. 45, 1835 ff. (1980) in succession with n-butyllithium/tetramethylethylenediamine, with carbon monoxide or ethyl chloroformate, and with hydrogen bromide, this being done according to the following equation:

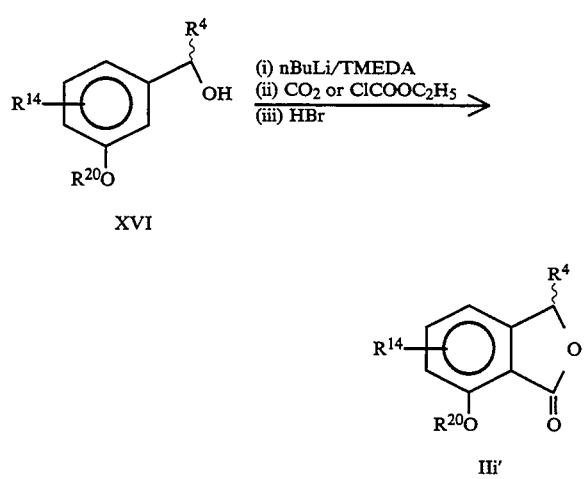

The starting materials of formula IX either are known or can be prepared by methods known per se.

Those starting materials of formula II wherein W is a group a) and $R^3$ is chlorine or bromine can be prepared by halogenation of the corresponding starting materials of formula II wherein $R^3$ is hydroxy, for example the starting materials of formulae IIb and IIe indicated above. Suitable halogenating agents (chlorinating or brominating agents) are especially the corresponding thionyl halide $SOHal'_2$, phosphorus oxyhalide $POHal'_3$, phosphorus trihalide $PHal'_3$ or phosphorus pentahalide $PHal'_5$ in each of which $Hal'$ is chlorine or bromine. A further method for the preparation of such chorine- or bromine-containing starting materials of formula II comprises treating the corresponding starting materials II wherein $R^3$ is hydrogen, for example the starting materials of formula IIi indicated above, with N-chloro- or N-bromo-succinimide. In order to obtain the starting materials of formula II wherein W is a group a) and $R^3$ is fluorine, $C_{1-6}$alkylthio, cyano or thiocyano, the corresponding starting materials of formula II wherein $R^3$ is chlorine or bromine can be subjected to a halogen-exchange reaction, for example with an alkali metal fluoride such as potassium fluoride, with a sodium mercaptide, with sodium cyanide or with potassium thiocyanate, respectively. All of these conversions can be carried out under reaction conditions that are known per se.

Those starting materials of formula II wherein W is a group a) and $R^3$ is cyano can also be prepared by treating a corresponding starting material of formula II wherein $R^3$ is hydroxy, for example a starting material of formula IIb or IIe indicated above, with potassium cyanide or hydrocyanic acid, this being carried out under reaction conditions known per se [see, for example, J. N. Frescos et al., J. Org. Chem. 50, 805 ff. (1985)].

Those compounds of formula II wherein W is a group a) and $R^3$ is $C_{2-7}$carboxyalkyl (example of "unsubstituted or substituted $C_{1-6}$alkyl"), carboxy or carbamoyl can be prepared by conventional hydrolysis of the corresponding compounds II wherein $R^3$ is ($C_{2-5}$alkoxycarbonyl)-$C_{1-6}$alkyl, $C_{2-7}$alkoxycarbonyl or cyano, respectively.

Those compounds of formula II wherein W is a group a) and $R^3$ is formyloxy, $C_{2-5}$alkanoyloxy, $C_{2-5}$alkoxycarbonyloxy, $C_{2-3}$alkylcarbamoyloxy or di($C_{1-2}$alkyl)carbamoyloxy can be prepared by conventional formylation, acylation, carbonylation or carbamoylation, respectively, of the corresponding compounds II wherein $R^3$ is hydroxy.

Finally, those compounds of formula II wherein W is a group a) and $R^3$ is di($C_{1-2}$alkoxy)phosphonyl can be prepared by reacting the corresponding compounds II wherein $R^3$ is hydroxy with a $C_{1-2}$alkyl phosphite.

Those starting materials of formula II wherein W is a group b), $Y^1$ and $Y^2$ are both oxygen and $R^6$ is hydrogen can be prepared, for example, according to the following Reaction Scheme 3, wherein $R^5$, $R^{14}$ and $R^{16}$ are as defined above and $R^{21}$ and $R^{22}$ are each methoxy or ethoxy.

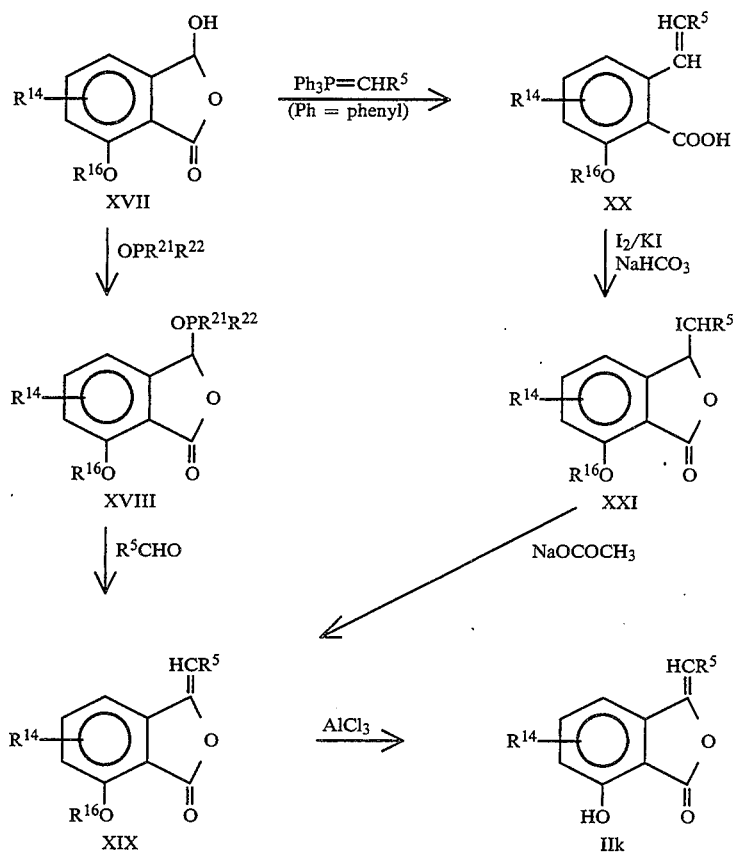

Reaction Scheme 3

An analogous reaction scheme, in which the individual reaction steps are illustrated, is described in R. S. Mali and S. L. Patil, Synthetic Comm. 20, 167 ff. (1990) and in E. Napolitano et al., Syntheses 1985, 38–40.

Those starting materials of formula II wherein W is a group c) and X and $Y^1$ are oxygen can be prepared in a manner known per se, for example in accordance with the methods of N. S. Narasimhan and B. H. Bhide, Tetr. 27, 6171 (1971), J. Sinha et al., J. Ind. Chem. Soc. 63, 907 (1986) and H. N. Singh and R. P. Singh, J. Ind. Chem. Soc. 65, 685 (1988) and also in accordance with the following Reaction Scheme 4:

Reaction Scheme 4

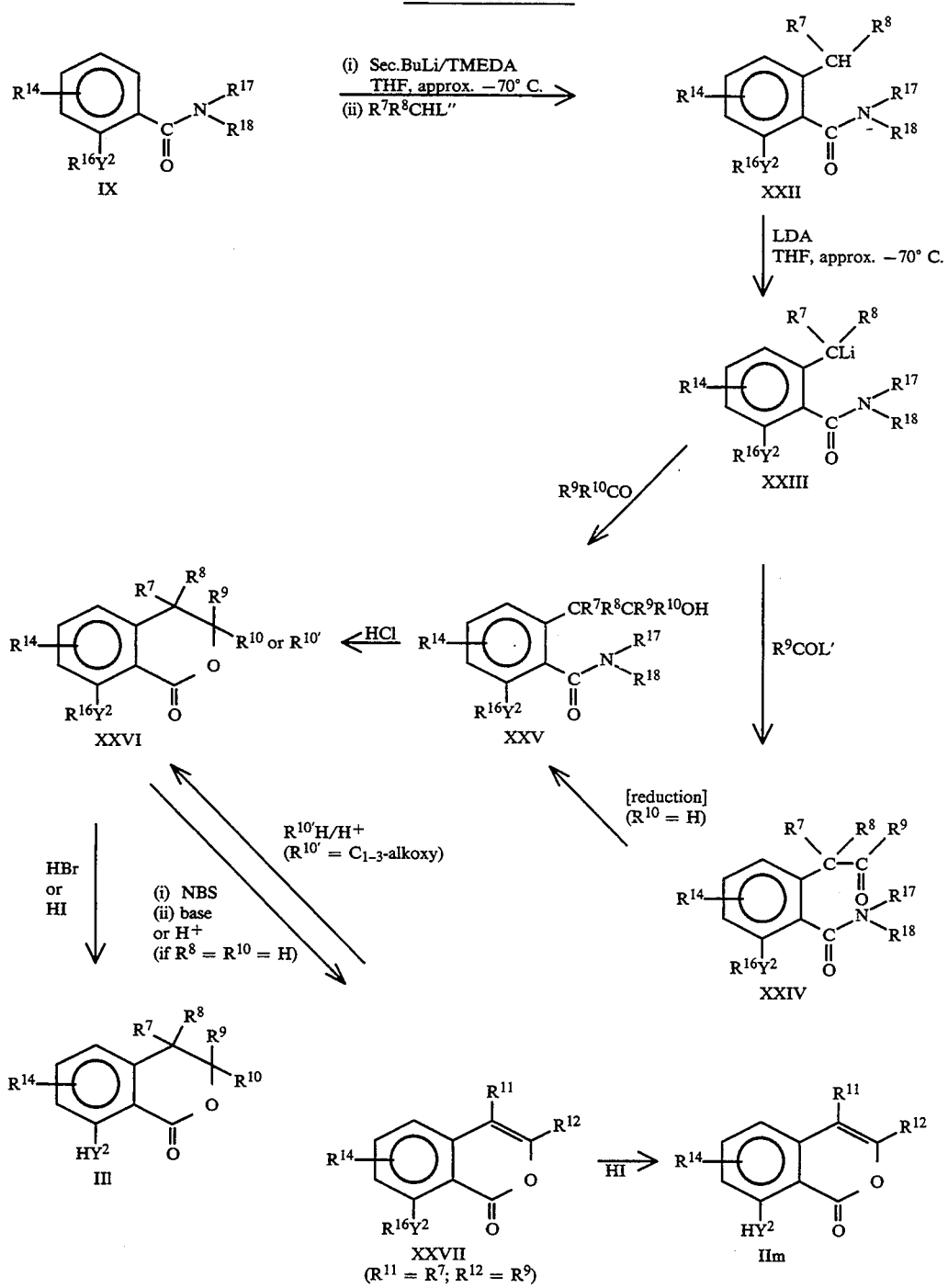

In that reaction scheme, $Y^2$, $R^7$, $R^8$, $R^9$, $R^{10}$, $R^{11}$, $R^{12}$, $R^{14}$, $R^{16}$, $R^{17}$, $R^{18}$, TMEDA THF and L' are as defined above and LDA denotes lithium diisopropylamide, NBS denotes N-bromosuccinimide and L" denotes a leaving group, such as halogen, especially chlorine, or 2-imidazolyl.

In that reaction scheme also, the individual reactions involved are known per se.

Those starting materials of formula II wherein W is a group d) and X and $Y^1$ are oxygen can be also prepared, for example, in accordance with the methods of N. L. Lewis et al., Synthesis 1986, 944 and F. M. Hauser et al., J. Org. Chem. 53, 4676 (1988).

In general, those starting materials of formula II wherein X and/or $Y^1$ are/is oxygen can be converted by sulfuration methods that are known per se [see, for example, N. Lozach, Sulfur Reports 9, 153 ff. (1980)] into the corresponding starting materials of formula II wherein X and/or $Y^1$ are/is sulfur. There is advantageously used for the sulfuration phosphorus pentasulfide, optionally in the presence of pyridine, for example in the form of the phosphorus pentasulfide-pyridine (1:2) complex, the Lawesson reagent 2,4-bis(4-methoxyphenyl)-1,2-dithioxo-1,3,2,4-dithiaphosphetan [see, for example, S.-O. Lawesson et al., Bull. Soc. Chim. Belg. 87, 229–238 (1978)] or the Davy reagent 2,4-bis(methylthio)-1,3,2,4-dithiadiphosphetan (see, for example, Sulfur Lett. 1983, 1, 167), this preferably being employed in a stoichiometric amount or in slight excess (for example up to 20%). The operation is advantageously carried out in an inert organic diluent, such as an unsubstituted or halogenated aromatic compound, for example toluene or dichlorobenzene, or an aliphatic or cyclic ether, for example dimethoxyethane, and at elevated temperature, especially at temperatures of from 80° C. to the reflux temperature of the reaction mixture. In addition, a catalytic amount, that is to say about from 0.1 to 10 per cent by weight based on the amount of the compound II, of hexamethylphosphoric acid triamide is advantageously added. This process is especially suitable for the preparation of those compounds of formula II wherein X is oxygen and $Y^1$ is sulfur.

Those starting materials of formula II wherein X is sulfur and $Y^1$ is oxygen can also be prepared, for example, by converting a hydroxy compound of formula XII (see Reaction Scheme 2) or XXV (see Reaction Scheme 4) or a compound of formula XXII (see Reaction Scheme 4) into the corresponding thio compound in accordance with the conversion reactions known to one skilled in the art, such as halogenation and sulfuration, and then lactonising the latter compound to give the compound of formula II:

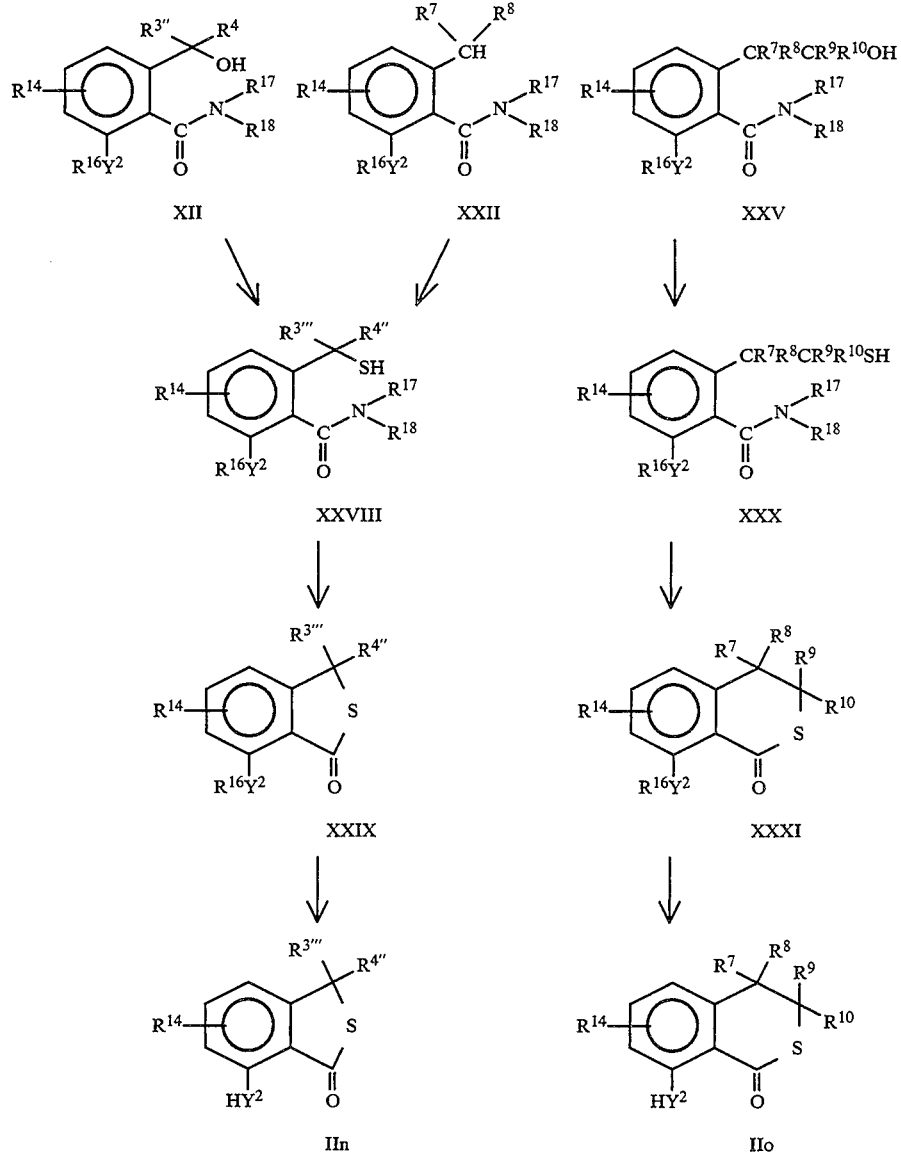

Reaction Scheme 5

In that Reaction Scheme, $R^{3''''}$ and $R^{4''}$ of the compound XXVIII are $R^{3''}$ and $R^4$ or $R^7$ and $R^8$, depending upon whether a compound of formula XII or a compound of formula XXII is used as starting material.

Those starting materials of formula II wherein $Y^2$ is sulfur—if not already obtainable by the methods described hereinbefore (see, for example, Reaction Schemes 2, 4 and 5)—can be prepared in a manner known per se, for example in accordance with the following Reaction Scheme 6 wherein W, X, $Y^1$ and $R^{14}$ are as defined above:

Reaction Scheme 6

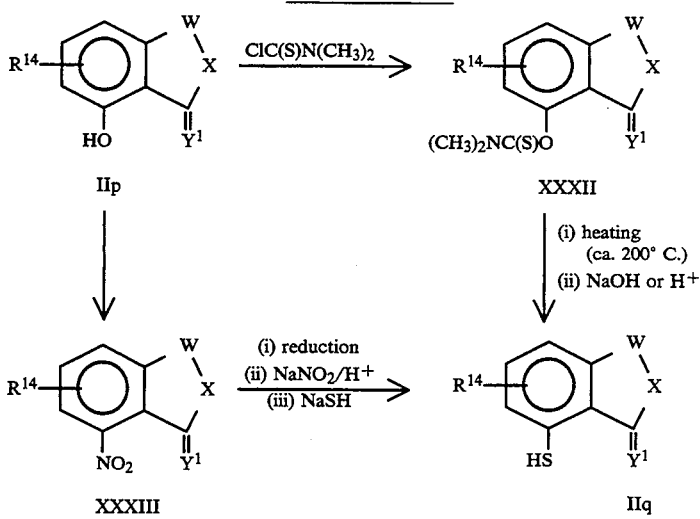

In the above Reaction Schemes 1-6 and equations (XV→IIb; XVI→IIi'), the products of formulae IIa–IIq are subgroups of starting materials of formula II. The starting materials of formulae IV, V, IX, XV, XVI and XVII either are known or can be prepared by methods that are known per se.

The starting materials of formula III are known for the most part, and the novel starting materials III can be prepared analogously to the known starting materials III.

The compounds of formula I (hereinafter referred to as compounds or active ingredients according to the invention) have herbicidal properties and are suitable for controlling weeds, including grass weeds, inter alia Agropyron repens, Alopecurus myosuroides, Avena fatua, Bromus inermis, Echinochloa crus-galli, Poa annua, Sorghum halepense, Abutilon theophrasti, Amaranthus retroflexus, Cassia obtusifolia, Chenopodium album, Galium aparine, Matricaria chamomilla, Sinapis arvensis and Stellaria media, in various crops of useful plants, inter alia rice (especially paddy), wheat, maize, soybean, rape and cotton crops. In addition, the compounds are both pre-emergence and post-emergence herbicides. Some representatives of the compounds I have been found to have good selectivity, for example in the control of weeds and grass weeds in soybean and cotton crops.

The compounds according to the invention furthermore have plant-growth-regulating properties and are suitable as active ingredients for positively influencing the growth of useful plants. This effect is able to bring about both desired growth inhibition in crop plants and sufficient inhibition of weeds after their germination to prevent them from competing with the crop plants. From an ecological standpoint this is an advantage and therefore is extremely desirable. In this connection, special mention should be made of protection of the soil surface from drying-out and/or erosion and the reduction of the supply of weed seeds in the soil (with the simultaneous prevention of flowering and renewed seeding). This effect is therefore to be preferred in certain circumstances to complete prevention of weed germination which may, however, be of limited duration.

In practice, a concentration of from 1 g to 3 kg of compound according to the invention/ha, preferably from 10 g to 1 kg of compound according to the invention/ha, is usually sufficient to achieve the desired herbicidal effect. In order to achieve the desired herbicidal effect with optimum tolerance by useful plants, the range of from 10 to 100 g/ha for pre-emergence treatment and of from 100 to 1000 g/ha for post-emergence treatment is especially beneficial.

The weed control composition and plant-growth-regulating composition according to the invention is characterised in that it comprises an effective amount of at least one compound of formula I, as defined above, and also formulation adjuvants. The composition advantageously comprises at least one of the following formulation adjuvants from among the group: solid carriers; solvents or dispersants; surfactants (wetting agents and emulsifiers); dispersants (without surface-active action); and stabilisers. Using these and other adjuvants, these compounds, that is to say the herbicidal active ingredients, can be converted into the customary formulations, such as dusts, powders, granules, solutions, emulsions, suspensions, emulsifiable concentrates, pastes and the like.

The compounds of formula I are generally water-insoluble and can be formulated in accordance with the methods customary for water-insoluble compounds using the relevant formulation adjuvants. The compositions may be prepared in a manner known per se, for example by mixing the respective active ingredient with solid carriers, by dissolving or suspending it in suitable solvents or dispersants, possibly with the use of surfactants as wetting agents or emulsifiers and/or of dispersants, by dilution of previously prepared emulsifiable concentrates with solvents or dispersants, etc..

Suitable solid carriers are essentially: natural mineral substances, such as chalk, dolomite, limestone, aluminas and silicic acid and salts thereof (for example diatomaceous earth, kaolin, bentonite, talcum, attapulgite and montmorillonite); synthetic mineral substances, such as highly dispersed silicic acid, aluminium oxide and silicates; organic substances, such as cellulose, starch, urea and synthetic resins; and fertilisers, such as phosphates and nitrates, it being possible for such carriers to be, for example, in the form of powders or in the form of granules.

Suitable solvents and dispersants are essentially: aromatic compounds, such as benzene, toluene, xylenes and alkylnaphthalenes; chlorinated aromatic compounds and chlorinated aliphatic hydrocarbons, such as chlorobenzenes, chloroethylenes and methylene chloride; aliphatic hydrocarbons, such as cyclohexane and paraffins, for example mineral oil fractions; alcohols, such as butanol and glycol, and their ethers and esters; ketones, such as acetone, methyl ethyl ketone, methyl isobutyl ketone and cyclohexanone; and strongly polar solvents and dispersants, such as dimethylformamide, N-methylpyrrolidone and dimethyl sulfoxide, such solvents preferably having flash points of at least 30° C. and boiling points of at least 50° C., and water. Among the solvents and dispersants there are also suitable so-called liquefied gaseous extenders or carriers, which are products that are gaseous at room temperature and under normal pressure. Examples of such products are especially aerosol propellant gases, such as halogenated hydrocarbons, for example dichlorodifluoromethane. If the weed control composition according to the invention is in the form of a pressurised gas pack, a solvent is advantageously used in addition to the propellant gas.

The surfactants (wetting agents and emulsifiers) may be non-ionic compounds, such as condensation products of fatty acids, fatty alcohols or fatty-substituted phenols with ethylene oxide; fatty acid esters and ethers of sugars or polyhydric alcohols; the products obtained from sugars or polyhydric alcohols by condensation with ethylene oxide; block polymers of ethylene oxide and propylene oxide; or alkyldimethylamine oxides.

The surfactants may also be anionic compounds, such as soaps; fatty sulfate esters, for example dodecyl sodium sulfate, octadecyl sodium sulfate and cetyl sodium sulfate; alkylsulfonates, arylsulfonates and fatty aromatic sulfonates, such as alkylbenzenesulfonates, for example calcium dodecylbenzenesulfonate, and butylnaphthalenesulfonates; and more complex fatty sulfonates, for example the amide condensation products of oleic acid and N-methyltaurin and the sodium sulfonate of dioctyl succinate.

Finally, the surfactants may be cationic compounds, such as alkyldimethylbenzylammonium chlorides, dialkyldimethylammonium chlorides, alkyltrimethylammonium chlorides and ethoxylated quaternary ammonium chlorides.

Suitable dispersants (without a surface-active action) are essentially: lignin, sodium and ammonium salts of lignosulfonic acids, sodium salts of maleic anhydride/diisobutylene copolymers, sodium and ammonium salts of sulfonated polycondensation products of naphthalene and formaldehyde, and sulfite liquors.

As dispersants that are especially suitable as thickening agents or anti-settling agents there may be used, for example, methylcellulose, carboxymethylcellulose, hydroxyethylcellulose, polyvinyl alcohol, alginates, caseinates and blood albumin.

Examples of suitable stabilisers are acid-binding agents, for example epichlorohydrin, phenyl glycidyl ethers and soya epoxides; antioxidants, for example gallic acid esters and butylhydroxytoluene; UV-absorbers, for example substituted benzophenones, diphenylacrylic acid esters and cinnamic acid esters; and deactivators, for example salts of ethylenediaminotetraacetic acid and polyglycols.

In addition to comprising the active ingredients according to the invention, the weed control compositions according to the invention may comprise synergistic substances and other active ingredients, for example insecticides, acaricides, fungicides, plant-growth regulators and fertilisers. Such combination compositions are suitable for increasing the activity and/or for broadening the activity spectrum.

The weed control compositions according to the invention generally comprise from 0.001 to 95% by weight, preferably from 0.5 to 75% by weight, of one or more compounds according to the invention as active ingredient(s). They may, for example, be in a form suitable for storage and transport. In such formulations, for example emulsifiable concentrates, the active ingredient concentration is normally in the higher range, preferably from 1 to 50% by weight, especially from 5 to 30% by weight. These formulations can then be diluted, for example with the same or different inert substances, to give active ingredient concentrations that are suitable for practical use, that is to say preferably approximately from 0.001 to 10% by weight, especially approximately from 0.005 to 5% by weight. The active ingredient concentration may also be lower or higher, however.

As mentioned above, the weed control compositions according to the invention can be prepared in a manner known per se.

For the preparation of powder compositions, the active ingredient, that is to say at least one compound according to the invention, can be mixed with a solid carrier, for example by grinding the two together; or the solid carrier can be impregnated with a solution or suspension of the active ingredient and the solvent or dispersant can then be removed by evaporation, heating or filtering with suction under reduced pressure. By adding surfactants or dispersants, such powder compositions can be made easily wettable with water so that they can be converted into aqueous suspensions that are suitable, for example, as spray compositions.

The active ingredient can also be mixed with a surfactant and a solid carrier to form a wettable powder that can be dispersed in water, or it can be mixed with a solid pregranulated carrier to produce a product in the form of granules.

If desired, the active ingredient can be dissolved in a water-immiscible solvent, such as, for example, a high-boiling hydrocarbon, that advantageously contains an emulsifier dissolved therein, so that the solution has a self-emulsifying action when water is added. Alternatively, the active ingredient can be mixed with an emulsifier and the mixture can then be diluted with water to the desired concentration. In addition, the active ingredient can be dissolved in a solvent and then mixed with an emulsifier. Such a mixture can also be diluted with water to the desired concentration. In this manner, emulsifiable concentrates or ready-for-use emulsions are obtained.

The use of the weed control compositions according to the invention, to which the present invention further relates, can take place according to customary methods of application, such as spraying, dusting, pouring or scattering. The method according to the invention for the control of weeds comprises treating the crop to be protected from weeds and/or the weeds with a compound according to the invention or with a weed control composition according to the invention.

The following Examples serve to illustrate the invention in detail.

I. PREPARATION OF THE COMPOUNDS OF FORMULA I

EXAMPLE 1

7-[(4,6-dimethoxy-pyrimidin-2-yl)oxy]-3-methyl-phthalide

A mixture of 0.4 g of 7-hydroxy-3-methyl-phthalide, 0.52 g of 4,6-dimethoxy-pyrimidin-2-ylmethylsulfone and 1.05 g of potassium carbonate is heated at reflux temperature in 5 ml of dimethylformamide for 2 hours. The mixture is then diluted with ethyl acetate and washed once with water and once with sodium chloride solution. The crude product which remains after evaporation of the solvent is purified by chromatography on silica gel using ethyl acetate/n-hexane (1:2) to yield 7-[(4,6-dimethoxy-pyrimidin-2-yl)oxy]-3-methyl-phthalide, m.p. 190°–191° C.; IR spectrum (CHCl$_3$): C=O 1765 cm$^{-1}$; $^1$H-NMR (CDCl$_3$, 200 MHz): 7.84 ppm (double-d, J$_1$=J$_2$=8 Hz, 1H), 7.57 ppm (d, J=8 Hz, 1H), 7.37 ppm (d, J=8 Hz, 1H), 6.01 ppm (s, 1H), 5.72 ppm (q, J=7 Hz, 1H), 3.73 ppm (s, 6H of the two OCH$_3$), 1.56 ppm (d, J=7 Hz, 3H).

EXAMPLE 2–81

Analogously to the process described in Example 1 (but in some cases acetonitrile or tetrahydrofuran being used as solvent and sodium hydride being used as base) the corresponding compounds of formulae II and III are reacted with each other to prepare the compounds of formula I listed in the following Tables 1–5:

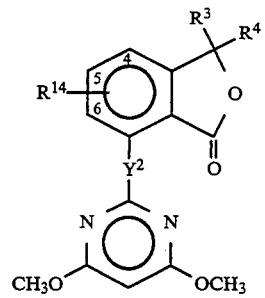

TABLE 1

| Example | R$^3$ | R$^4$ | Y$^2$ | R$^{14}$ | physical data |
| --- | --- | --- | --- | --- | --- |
| 2 | H | H | O | H | m.p. 238° C.; IR(CHCl$_3$): C=O 1760 cm$^{-1}$ |
| 3 | ethyl | H | O | H | m.p. 159–161° C.; IR(CHCl$_3$): C=O 1765 cm$^{-1}$ |
| 4 | isopropyl | H | O | H | m.p. 124–126° C.; IR(CHCl$_3$): C=O 1764 cm$^{-1}$ |
| 5 | methyl | methyl | O | H | m.p. 154–156° C.; |
| 6 | ethyl | methyl | O | H | m.p. 115° C.; IR(CHCl$_3$): C=O 1760 cm$^{-1}$ |
| 7 | phenyl | H | O | H | m.p. 170–173° C. |
| 8 | methoxy | H | O | H | m.p. 129–130° C.; IR(CHCl$_3$): C=O 1760 cm$^{-1}$ |
| 9 | isopropoxy | H | O | H | m.p. 120–122° C.; IR(CHCl$_3$): C=O 1770 cm$^{-1}$ |
| 10 | benzyloxy | H | O | H | m.p. 130–132° C. |
| 11 | tert-butoxy | H | O | H | m.p. 125–127° C. |
| 12 | methyl | H | S | H | m.p. 159–160° C. |
| 13 | ethoxy | H | O | H | m.p. 97–98° C. |
| 14 | methyl | H | O | 6-methyl | m.p. 145–147° C. |
| 15 | methoxy | methyl | O | H | m.p. 114–115° C. |
| 16 | H | methyl | O | H | (R-isomer) [α]$_{20}^D$ +10.19° |
| 17 | carbamoyl | H | O | H | m.p. 240° C. (with decomposition) |
| 18 | trifluoromethyl | H | O | H | m.p. 162–164° C. |
| 19 | 2-chloroethoxy | H | O | H | m.p. 93–95° C. |
| 20 | propargyloxy | H | O | H | m.p. 125–128° C. |
| 21 | n-propoxy | H | O | H | m.p. 99–100° C. |
| 22 | 2-methoxy-ethoxy | H | O | H | m.p. 95–96° C. |
| 23 | methyl | H | O | 4-chloro | m.p. 145–148° C. |
| 24 | methyl | H | O | 4-bromo | m.p. 147–149° C. |
| 25 | n-propyl | H | O | H | m.p. 94–95° C. |
| 26 | n-butyl | H | O | H | m.p. 94–95° C. |
| 27 | ethynyl | H | O | H | |
| 28 | nitromethyl | H | O | H | m.p. 150–152° C. |
| 29 | methoxy-carbonyl | H | O | H | |
| 30 | fluoro | H | O | H | |
| 31 | 2-dimethyl-aminoethoxy | H | O | H | |
| 32 | 2-methylthio-ethoxy | H | O | H | |
| 33 | n-butoxy | H | O | H | |

TABLE 1-continued

| Example | R³ | R⁴ | Y² | R¹⁴ | physical data |
|---|---|---|---|---|---|
| 34 | (N-methylcar-bamoyl)methoxy | H | O | H | |
| 35 | acetyloxy | H | O | H | |
| 36 | ethoxycarbon-yloxy | H | O | H | |
| 37 | hydroxy | trifluoro-methyl | O | H | m.p. 234–235° C. |

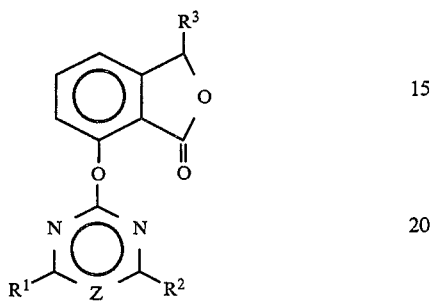

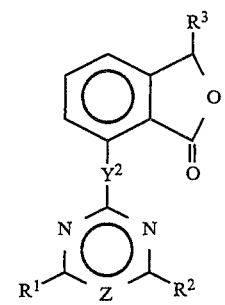

TABLE 3

| Example | Y² | R¹ | R² | R³ | physical data |
|---|---|---|---|---|---|
| 58 | O | methoxy | methoxy | methyl | m.p. 133–134° C. |
| 59 | O | methoxy | methoxy | methoxy | m.p. 88–90° C. |
| 60 | S | methoxy | methoxy | methyl | m.p. 150–151° C. |
| 61 | O | chloro | methyl | methyl | m.p. 144–147° C. |
| 62 | O | methoxy | dimethyl-amino | methyl | m.p. 148–151° C. |
| 63 | O | methyl | methoxy | methyl | m.p. 148–151° C. |
| 64 | O | methoxy | methyl-amino | methyl | m.p. 179–182° C. |
| 65 | O | chloro | methyl- | methyl | m.p. 181–183° C. |

TABLE 2

| Example | Z | R¹ | R² | R³ | physical data |
|---|---|---|---|---|---|
| 38 | CH | methyl | methyl | methyl | m.p. 163–164° C.; IR(CHCl₃): C=O 1770 cm⁻¹ |
| 39 | CH | ethoxy | ethoxy | methyl | m.p. 99–100° C.; IR(CHCl₃): C=O 1765 cm⁻¹ |
| 40 | CH | methoxy | methyl | methyl | m.p. 149–149° C.; IR(CHCl₃): C=O 1765 cm⁻¹ |
| 41 | C-Cl | methoxy | methoxy | methyl | m.p. 195–196° C. |
| 42 | CH | trifluoro-methyl | methoxy | methyl | m.p. 114–117° C. |
| 43 | CH | chloro | methoxy | methyl | m.p. 149–150° C. |
| 44 | CH | isopro-poxy | methoxy | methyl | m.p. 79–82° C. |
| 45 | CH | methoxy | methyl | methoxy | m.p. 107° C. |
| 46 | CH | n-pro-poxy | methoxy | methyl | m.p. 108–109° C. |
| 47 | CH | chloro | difluoro-methoxy | methyl | m.p. 114–117° C. |
| 48 | CH | chloro | dimethyl-amino | methyl | m.p. 180–183° C. |
| 49 | CH | methyl | 2,2,2-tri-fluoro-ethoxy | methyl | m.p. 79–81° C. |
| 50 | CH | chloro | methyl-amino | methyl | m.p. 185–188° C. |
| 51 | CH | H | methoxy | methyl | m.p. 110–112° C. |
| 52 | CH | methoxy | ethoxy | methyl | m.p. 113–116° C. |
| 53 | CH | chloro | methoxy | methoxy | m.p. 114–115° C. |
| 54 | CH | methoxy-methyl | methoxy | methyl | m.p. 76–78° C. |
| 55 | CH | difluoro-methoxy | methoxy | methyl | m.p. 108–109° C. |
| 56 | CH | methoxy | n-methoxy-methyl-amino | methyl | m.p. 106–108° C. |
| 57 | CH | methoxy | ethyl-amino | methyl | m.p. 143–146° C. |

TABLE 3-continued

| Example | Y² | R¹ | R² | R³ | physical data |
|---|---|---|---|---|---|
| 66 | O | methoxy | amino methoxy | ethyl | m.p. 137–140° C. |
| 67 | O | chloro | methoxy | methyl | m.p. 139–142° C. |

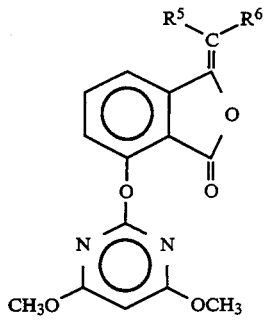

TABLE 4

| Example | R⁵ | R⁶ | physical data |
|---|---|---|---|
| 68 | methyl | H | m.p. 165–167° C.; (Z) IR (CHCl₃): C=O 1765 cm⁻¹ ¹H-NMR (CDCl₃): 5.69 ppm (q, J=7Hz, CH=) |
| 69 | methyl | methyl | m.p. 193–196° C.; (Z) IR (CHCl₃): C=O 1768 cm⁻¹ |
| 70 | 4-methoxy-phenyl | H | m.p. 231–233° C.; (E) ¹H-NMR (CDCl₃): 6.99 ppm (s, CH=) |
| 71 | phenyl | H | m.p. 191–192° C.; (Z) ¹H-NMR (CDCl₃): 6.46 ppm (s, CH=) (Z) |
| 72 | 3-methoxy-phenyl | H | m.p. 144–147° C.; (Z) ¹H-NMR (CDCl₃): 6.43 ppm (s, CH=) |
| 73 | ethyl | H | m.p. 122–125° C.; (Z) ¹H-NMR (CDCl₃): 5.64 ppm (t, J=7Hz, CH=) |
| 74 | n-propyl | H | m.p. 115–118° C.; (Z) ¹H-NMR (CDCl₃): 5.66 ppm (t, J=8Hz, CH=) |
| 75 | H | H | |

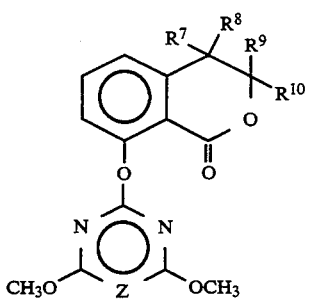

TABLE 5

| Example | Z | —CR⁷R⁸—CR⁹R¹⁰— | physical data |
|---|---|---|---|
| 76 | CH | —CH₂CH(CH₃)— | m.p. 180–182° C.: IR(CHCl₃): C=O 1728 cm⁻¹ |
| 77 | N | —CH₂CH(CH₃)— | m.p. 140–143° C. |
| 78 | CH | —CH₂CH(C₂H₅)— | m.p. 78–80° C. |
| 79 | CH | —CH(CH₃)CH(CH₃)— | (trans-form) ¹H-NMR (CDCl₃): 4.38 ppm (m, 1H) |
| 80 | CH | CH(CH₃)CH(CH₃)— | (cis-form) ¹H-NMR (CDCl₃): 4.68 ppm (m, 1H) |
| 81 | CH | CH(CH₃)CH₂— | m.p. 116–119° C. |

EXAMPLE 82

8-[(4,6-dimethoxy-pyrimidin-2-yl)oxy]-3-methyl-isochromen-1-one

Analogously to the process described in Example 1, 8-hydroxy-3-methyl-isochromen-1-one is reacted with 4,6-dimethoxypyrimidin-2-ylmethylsulfone to prepare 8-[(4,6-dimethoxy-pyrimidin-2-yl)oxy]-3-methyl-isochromen-1-one, m.p. 188°–190° C.

EXAMPLE 83

3-[(Z)-ethylidene]-7-[(4,6-dimethoxy-pyrimidin-2-yl)oxy]-phthalide 350 mg (2 mmol) of 7-hydroxy-3-vinyl-phthalide, 460 mg (2.2 mmol) of 4,6-dimethoxy-2-methylsulfonyl-pyrimidine and 414 mg (3 mmol) of potassium carbonate are heated in 10 ml of dimethylformamide for 1 hour at 100° C. The reaction mixture is then poured onto 100 ml of semi-concentrated sodium chloride solution and the aqueous mixture is extracted twice with 50 ml of ethyl acetate. The organic phase is dried over anhydrous magnesium sulfate and concentrated under reduced pressure and the crude product is subjected to purification by chromatography on silica gel using ethyl acetate/n-hexane (2:3).

In this manner, there are obtained 250 mg of 3-[(Z)-ethylidene]-7-[(4,6-dimethoxy-pyrimidin-2-yl)oxy]-phthalide in the form of colourless crystals, m.p. 163°–165° C.; IR spectrum (CHCl₃): C=O 1765 cm⁻¹. This product is identical to the compound of Example 68.

EXAMPLE 84

7-[(4,6-dimethoxy-pyrimidin-2-yl)oxy]-3-hydroxy-phthalide a) 15.2 g of 7-[(4,6-dimethoxy-pyrimidin-2-yl)oxy]-3-methoxyphthalide (see Example 8) are heated at reflux temperature in a 1:1 mixture of tetrahydrofuran and hydrochloric acid for 3 hours. Concentration is then carried out under reduced pressure and the resulting crystals are filtered off and washed with water to yield pure 7-[(4,6-dimethoxy-pyrimidin-2-yl)oxy]-3-hydroxy-phthalide, m.p. 143°–145° C.; IR (KBr): 1770 cm⁻¹; ¹H-NMR (CDCl₃): 6.60 ppm (s, 1H).

b) The above-mentioned product can also be prepared by dissolving 6 g of 3,7-dihydroxy-phthalide in a methanolic solution of 2.6 g of potassium hydroxide and concentrating a resulting solution to dryness by evaporation azeotropically with toluene. The mono-potassium salt is then taken up in 100 ml of dry dimethyl sulfoxide and treated in portions with 1.9 g of sodium hydride. Stirring is then continued for 10 minutes at 40° C., 9.9 g of 4,6-dimethoxy-pyrimidinyl-2-methylsulfone are then added at room temperature and the reaction mixture is maintained at from 30° to 35° C. for a further hour. Water is added and the mixture is extracted with ethyl acetate in order to remove impurities. The aqueous phase is acidified with hydrochloric acid and then extracted with fresh ethyl acetate to yield, after treatment with activated carbon and/or filtration on silica gel, 7-[(4,6-dimethoxy-pyrimidin-2-yl)oxy]-3-hydroxy-phthalide in the form of slightly yellowish crystals, m.p. 144°–146° C.

EXAMPLE 85

3-chloro-7-[(4,6-dimethoxy-pyrimidin-2-yl)oxy]-phthalide 2.3 g of 7-[(4,6-dimethoxy-pyrimidin-2-yl)oxy]-3-hydroxy-phthalide (see Example 84) are suspended in approximately 40 ml of phosphorus oxychloride, and the suspension is heated at 90° C. for 2 hours. The reaction mixture is then introduced at from 35° to 45° C. into 250 ml of water. It is then diluted with a further 500 ml of water and the crystals which separate are filtered off and washed neutral with water to yield pure 3-chloro-7-[(4,6-dimethoxy-pyrimidin-2-yl)oxy]-phthalide in the form of slightly yellowish crystals, m.p. 143°–144° C.

EXAMPLE 86

7-[(4,6-dimethoxy-pyrimidin-2-yl)oxy]-3-fluoro-phthalide

A mixture of 1.0 g of 3-chloro-7-[(4,6-dimethoxy-pyrimidin-2-yl)oxy]-phthalide (see Example 85) and 0.19 g of spray-dried potassium fluoride and a spatula tip of 18-crown-6 is heated at reflux temperature for 100 minutes. The mixture is then filtered over Celite ® and is concentrated by evaporation, and the crude product is recrystallised from ethyl acetate/n-hexane to yield 7-[(4,6-dimethoxy-pyrimidin-2-yl)oxy]-3-fluoro-phthalide, m.p. 172°–174° C.

EXAMPLE 87

7-[(4,6-dimethoxy-pyrimidin-2-yl)oxy]-3-methylthio-phthalide 1.0 g of 3-chloro-7-[(4,6-dimethoxy-pyrimidin-2-yl)oxy]-phthalide (see Example 85) and 0.24 g of sodium methyl-mercaptide are stirred in 20 ml of tetrahydrofuran for approximately 16 hours. The mixture is then filtered through Celite ® and concentrated by evaporation under reduced pressure. Recrystallisation from diethyl ether/n-hexane yields 7-[(4,6-dimethoxy-pyrimidin-2-yl)oxy]-3-methylthio-phthalide, m.p. 138°–140° C.

EXAMPLE 88

3-ethylthio-7-[(4,6-dimethoxy-pyrimidin-2-yl)oxy]-phthalide

Analogously to the method described above (Example 87), there is obtained from 3-chloro-7-[(4,6-dimethoxypyrimidin-2-yl)oxy]-phthalide (see Example 85) and sodium ethylmercaptide 3-ethylthio-7-[(4,6-dimethoxy-pyrimidin-2-yl)oxy]-phthalide, m.p. 103°–106° C.

EXAMPLE 89

7-[(4,6-dimethoxy-pyrimidin-2-yl)oxy]-3-thiocyano-phthalide

A mixture of 1.4 g of 3-chloro-7-[(4,6-dimethoxy-pyrimidin-2-yl)oxy]-phthalide (see Example 85) and 0.46 g of potassium thiocyanate is heated in the presence of a spatula tip of 18-crown-6 in 15 ml of acetonitrile for 4 hours. The mixture is then filtered through Celite ®, concentrated by evaporation and chromatographed with 30% ethyl acetate/n-hexane to yield 7-[(4,6-dimethoxy-pyrimidin-2-yl)oxy]-3-thiocyano-phthalide in the form of light-yellow crystals, m.p. 161°–163° C.

EXAMPLE 90

7-[(4,6-dimethoxy-pyrimidin-2-yl]oxy]-3-phenoxy-phthalide

A mixture of 1.4 g of 3-chloro-7-[(4,6-dimethoxy-pyrimidin-2-yl)oxy]-phthalide (see Example 85) and 0.63 g of potassium phenolate is heated at reflux temperature in the presence of a spatula tip of 18-crown-6 in 15 ml of acetonitrile. After 19 hours, the reaction mixture is filtered through Celite ® and concentrated by evaporation, and the crude product is purified by column chromatography (eluant 25% ethyl acetate/n-hexane) to yield 7-[(4,6-dimethoxy-pyrimidin-2-yl)oxy]-3-phenoxy-phthalide in the form of white crystals, m.p. 155°–157° C.

EXAMPLE 91

7-[(4,6-dimethoxy-pyrimidin-2-yl)oxy]-3-vinyl-phthalide 3.6 g of 7-[(4,6-dimethoxy-pyrimidin-2-yl)oxy]-3-hydroxy-phthalide (see Example 84) are placed in 60 ml of absolute tetrahydrofuran at −45° C., and the solution is treated within 10 minutes with 18 ml of a 2M solution of vinylmagnesium chloride solution in tetrahydrofuran. The reaction solution is then stirred for approximately 16 hours at room temperature, a further 6 ml of vinyl-magnesium chloride solution are added and the reaction solution is heated at reflux temperature for a further hour. When it has cooled, the reaction solution is acidified with 1N hydrochloric acid and freed of tetrahydrofuran in a rotary evaporator. The aqueous phase is then extracted with tert-butyl methyl ether, and the organic phase is washed and concentrated by evaporation under reduced pressure. Silica gel chromatography using ethyl acetate/n-hexane (2:3) as eluant yields pure 7-[(4,6-dimethoxy-pyrimidin-2-yl)oxy]-3-vinyl-phthalide, m.p. 94°–97° C.

EXAMPLE 92

3-cyano-7-[(4,6-dimethoxy-pyrimidin-2-yl)oxy]-phthalide 1.0 g of 7-[(4,6-dimethoxy-pyrimidin-2-yl)oxy]-3-hydroxy-phthalide (see Example 84) is introduced into a solution of 2.1 g of potassium cyanide in 15 ml of water and the whole is treated dropwise at from −7° to −3° C., with cooling, over a period of 10 minutes, with 10 ml of concentrated hydrochloric acid. It is subsequently stirred at room temperature for approximately 16 hours and the crystals which have separated are then filtered off. They are washed with water and recrystallised from acetone/n-hexane to yield 0.2 g of 3-carbamoyl-7-[(4,6-dimethoxy-pyrimidin-2-yl)oxy]-phthalide (see also Example 17).

The mother liquor is chromatographed using ethyl acetate/n-hexane (1:1) as eluant to yield pure 3-cyano-7-[(4,6-dimethoxy-pyrimidin-2-yl)oxy]-phthalide, m.p. 157°–159° C.

EXAMPLE 93

3-cyanomethoxy-7-[(4,6-dimethoxy-pyrimidin-2-yl)oxy]-phthalide

A mixture of 1.5 g of 7-[(4,6-dimethoxy-pyrimidin-2-yl)oxy]-3-hydroxy-phthalide (see Example 84) and 0.8 ml of chloroacetonitrile is maintained at 60° C. for 1 hour in ethyl methyl ketone in the presence of 2.1 g of dry potassium carbonate and a spatula tip each of sodium iodide and 18-crown-6. When the reaction material has cooled, it is taken up in tert-butyl methyl ether and the solution is washed with dilute hydrochloric acid and water, concentrated by evaporation and purified by chromatography on silica gel (eluant: ethyl acetate/n-hexane 1:1) to yield 3-cyanomethoxy-7-[(4,6-dimethoxypyrimidin-2-yl)oxy]-phthalide, m.p. 99°–102° C.

EXAMPLE 94

7-[(4,6-dimethoxy-pyrimidin-2-yl)oxy]-3-(methoxycarbonylmethoxy)-phthalide

Analogously to the method described above (Example 93), there is obtained from 7-[(4,6-dimethoxy-pyrimidin-2-yl)oxy]-3-hydroxy-phthalide (see Example 84) and chloroacetic acid methyl ester 7-[(4,6-dimethoxy-pyrimidin-2-yl)oxy]-3-(methoxycarbonylmethoxy)-phthalide, m.p. 102°–104° C.

EXAMPLE 95

3-acetoxy-7-[(4,6-dimethoxy-pyrimidin-2-yl(oxy]-phthalide 1.3 g of 7-[(4,6-dimethoxy-pyrimidin-2-yl)oxy]-3-hydroxy-phthalide (see Example 84) are dissolved in 30 ml of tetrahydrofuran, and 0.6 ml of triethylamine is added to the solution which is then treated dropwise at 25° C. (internal temperature) with 0.5 ml of acetyl chloride. After subsequently stirring for 2 hours at room temperature, the reaction mixture is treated with ice-water and dilute hydrochloric acid and extracted with ethyl acetate, and the organic phase is washed with sodium chloride solution, dried over anhydrous magnesium sulfate and concentrated by evaporation under reduced pressure. Column chromatography on silica gel [eluant: ethyl acetate/n-hexane (2:3)] yields 3-acetoxy-7-[(4,6-dimethoxy-pyrimidin-2-yl)oxy]-phthalide in the form of white crystals, m.p. 119°–120° C.

EXAMPLE 96

3-(ethoxycarbonylmethyl)-7-[(4,6-dimethoxy-pyrimidin-2-yl]oxy]-phthalide

A mixture of 1.5 g of 7-[(4,6-dimethoxy-pyrimidin-2-yl)oxy]-3-hydroxy-phthalide (see Example 84) and 2.5 g of (ethoxycarbonylmethylene)-triphenyl-phosphorane is maintained at reflux temperature for 10 hours in approximately 40 ml of tetrahydrofuran. The solvent is then evaporated off and the reaction material which remains is purified on a column of silica gel (eluant: ethyl acetate/n-hexane 1:1) to yield 3-(ethoxycarbonylmethyl)-7-[(4,6-dimethoxy-pyrimidin-2-yl)oxy]-phthalide, m.p. 150°–152° C.

EXAMPLE 97

3-(dimethoxyphosphonyl)-7-[(4,6-dimethoxy-pyrimidin-2-yl(oxy]-phthalide 1.0 g of 7-[(4,6-dimethoxy-pyrimidin-2-yl)oxy]-3-hydroxy-phthalide (see Example 84) is dissolved in 30 ml of methanol, 0.88 ml of 5.4M sodium methanolate solution is added and the whole is then treated dropwise with 0.43 ml of dimethyl phosphite. It is left at room temperature for one hour and then 0.33 ml of methanesulfonic acid is added and the reaction mixture is concentrated by evaporation under reduced pressure. The residue is taken up in ethyl acetate, and the solution is washed once with 2N hydrochloric acid and once with sodium chloride solution. The organic solution is treated with activated carbon and the product is recrystallised from ethyl acetate/n-hexane to yield 3-(dimethoxyphosphonyl)-7-[(4,6-dimethoxy-pyrimidin-2-yl)oxy]-phthalide, $^1$H-NMR (CDCl$_3$): 5.70 ppm (d, 11 Hz, 1H), 3.93 and 3.64 ppm (2d, 11 Hz, P(O) (OCH$_3$)$_2$); m.p. 135°–137° C.

EXAMPLE 98

7-[(4,6-dimethoxy-pyrimidin-2-yl)oxy]-3-methyl-2-benzothiophen-1(3H)]-one 1.21 g of 7-hydroxy-3-methyl-isobenzofuran-1(3H)-thione are heated at reflux temperature for 2 hours in 10 ml of acetonitrile together with 0.83 g of 4,6-dimethoxy-pyrimidinyl-2-methylsulfone and 1.05 g of potassium carbonate in the presence of a spatula tip of 18-crown-6.

The reaction material is taken up in ethyl acetate, and the organic solution is washed with water and sodium chloride solution, concentrated by evaporation under reduced pressure and then purified by chromatography (eluant 30% diethyl ether in n-hexane) to yield 7-[(4,6-dimethoxy-pyrimidin-2-yl)oxy]-3-methyl-2-benzothiophen-1(3H)-one in the form of yellowish crystals, m.p. 157°–159° C.; IR spectrum (CHCl$_3$): 1682, 1600, 1555, 1356, 1240, 1190 cm$^{-1}$; $^1$H-NMR (CDCl$_3$): 4.86 ppm (q, 1H), 1.78 ppm (d, 3H).

EXAMPLE 99

7-[(4-dimethoxy-pyrimidin-2-yl(oxy]-3-methyl-isobenzofuran-1(3H)-thione

A mixture of 6.35 g of 7-[(4,6-dimethoxy-pyrimidin-2-yl)oxy]-3-methyl-phthalide (see Example 1) and 8.92 g of 2,4-bis(4-methoxyphenyl)-2,4-dithioxo-1,3,2,4-dithiadiphosphetan (Lawesson reagent) is maintained at reflux temperature for approximately 16 hours in 40 ml of xylene. The reaction material is then filtered over silica gel (eluant: 30% diethyl ether/n-hexane) and recrystallised from ethyl acetate/n-hexane to yield 7-[(4,6-dimethoxy-pyrimidin-2-yl)oxy]-3-methyl-isobenzofuran-1(3H)-thione in the form of yellow crystals, m.p. 163°–164° C.; IR spectrum (CHCl$_3$): 1602, 1570, 1358, 1304, 1195 cm$^{-1}$; $^1$H-NMR (CDCl$_3$): 5.80 ppm (q, 1H), 1.71 ppm (d, 3H).

EXAMPLE 100

7-[(4,6-dimethoxy-(1,3,5-triazin-2-yl)oxy]-3-methyl-isobenzofuran-1(3)H-thione 1.0 g of 7-hydroxy-3-methyl-isobenzofuran-1(3H)-thione is introduced into a suspension of 0.15 g of sodium hydride in absolute dimethylformamide and, when the evolution of hydrogen has ceased, 1.0 g of 2-chloro-4,6-dimethoxy-1,3,5-triazine is added thereto. The reaction mixture is subsequently stirred at room temperature for 5 hours, ice-water is then added and the whole is extracted with ethyl acetate and washed with sodium chloride solution. The crude product, having been concentrated by evaporation, is purified by chromatography (eluant: 45% ethyl acetate in n-hexane) and recrystallised from acetone/n-hexane to yield 7-[(4,6-dimethoxy-1,3,5-triazin-2-yl)oxy]-3-methyl-isobenzofuran-1(3H)-thione in the form of yellow crystals, m.p. 177°–178° C.; IR spectrum (CHCl$_3$): 1590, 1560, 1366, 1304, 1140 cm$^{-1}$; $^1$H-NMR (CDCl$_3$): 5.81 ppm (q, 1H), 1.73 ppm (d, 3H).

II. PREPARATION OF THE STARTING MATERIALS OF FORMULA II

EXAMPLE 101

7-hydroxy-3-methyl-phthalide (i) 12.5 ml of methyllithium (1.6M in diethyl ether) are added dropwise within 30 minutes at −78° C. under argon to a solution of 5.32 g of 1-(2,2-dimethyl-propanoyloxy)-3,5-dioxo-exo-10-oxatricy-clo[5.2.1.0(2,6)]dec-8-ene (compound of formula VI wherein $R^{14'}$ is hydrogen and $R^{15}$ is 2,2-dimethyl-propanoyloxy) in 50 ml of absolute tetrahydrofuran. When the addition is complete, the reaction mixture is allowed to warm to room temperature and is then poured onto 100 ml of ice-cold saturated monopotassium phosphate solution. The aqueous solution is extracted three times with diethyl ether and the combined organic phases are washed with monopotassium phosphate solution, dried over anhydrous magnesium sulfate and, after being decolorised with activated carbon, are filtered and concentrated. The yellow-coloured crude product is recrystallised from diethyl ether/n-hexane to yield 1.8 g (32% of the theoretical yield) of (3aα,4β,7β,7aα)-hexahydro-1-hydroxy-1-methyl-3-oxo-4,7-epoxyisobenzofuran-4-yl pivalate in the form of yellowish crystals, m.p. 153°–154° C. (=compound of formula VIII wherein $R^{4'}$ is methyl, $R^{14'}$ is hydrogen and $R^{15}$ is 2,2-dimethylpropanoyloxy).

(ii) 1.7 g of the product of the preceding reaction step are added at from 2° to 4° C. under argon to a suspension of 0.31 g of sodium borohydride in 40 ml of absolute ethanol. When the addition is complete, the reaction mixture is allowed to warm to room temperature and is poured onto 60 ml of 1N hydrochloric acid. The ethanol is evaporated off under reduced pressure, and the resulting white crystals are filtered off, washed with water and dried to yield 0.87 g (86% of the theoretical yield) of (3aα,4β,7β,7aα)-hexahydro-1-methyl-3-oxo-4,7-epoxyisobenzofuran-4-yl pivalate in the form of colourless crystals, m.p. 114°–115° C.

(iii) 11.4 g of the product of the preceding reaction step are added in portions to 30 ml of concentrated sulfuric acid cooled with ethanol/ice. When the addition is complete, the mixture is poured onto ice, and the crystals which separate are then filtered and washed with water until neutral to yield 6.4 g (91% of the theoretical yield) of 7-hydroxy-3-methyl-phthalide in the form of beige crystals, m.p. 107°–108° C.

EXAMPLE 102

3,3-dimethyl-7-hydroxy-phthalide (i) A Grignard solution prepared from 1.43 g of magnesium and 8.37 g of methyl iodide in 65 ml of diethyl ether is added dropwise to a solution of 7.85 g of 1-(2,2-dimethylpropanoyloxy)-3,5-dioxo-exo-10-oxatricyclo[5.2.-1.0(2,6)]dec-8-ene in 35 ml of tetrahydrofuran in such a manner that the temperature does not exceed −25° C. When the addition is complete the reaction mixture is stirred at room temperature for a few more hours, is then acidified to pH 2 with 2N hydrochloric acid and extracted with diethyl ether. After drying of the ethereal solution and evaporation of the solvent, 7.5 g of crude product remain which are then purified by chromatography on silica gel using diethyl ether/n-hexane (3:1) to yield (3aα, 4β,7β,7aα)-hexahydro-1,1-dimethyl-3-oxo-4,7-epoxyisobenzofuran-4-yl pivalate in the form of an oil.

(ii) The oily product of the preceding reaction step is taken up in 2.8 ml of concentrated sulfuric acid, and the solution is stirred at 5° C. for 20 minutes. The solution is then poured onto ice and extracted with diethyl ether. The organic phase is washed with water, dried over anhydrous magnesium sulfate and concentrated by evaporation to yield 3,3-dimethyl-7-hydroxy-phthalide in the form of colourless crystals, m.p. 128°–134° C.

EXAMPLE 103

3-ethyl-7-hydroxy-phthalide (i) 13.7 ml of sec-butyllithium (1.4M in cyclohexane/isopentane) are added dropwise to a solution of 5.2 g of 2-methoxy-N,N-diethyl-benzamide and 2.91 g of tetramethylethylenediamine in 50 ml of absolute tetrahydrofuran in such a manner that the temperature does not exceed −68° C. When the addition is complete, the reaction mixture is stirred at −78° C. for a further hour and then 2.5 ml of propionaldehyde are added. The reaction mixture is allowed to warm slowly to room temperature, is subsequently stirred for one hour and is diluted with 300 ml of diethyl ether. The organic phase is washed with 2N hydrochloric acid and then with saturated sodium chloride solution, dried over anhydrous magnesium sulfate and concentrated by evaporation to yield 6-(1-hydroxyethyl)-2-methoxy-N,N-diethyl-benzamide in the form of a crude product.

(ii) The crude product of the preceding reaction step is taken up in 48% aqueous hydrogen bromide, and the solution is heated at reflux temperature for approximately 16 hours. The mixture is then cooled to room temperature and extracted twice with diethyl ether. After drying over anhydrous magnesium sulfate and concentration by evaporation, a crude product remains which is then purified by chromatography on silica gel using diethyl ether/n-hexane (1:4) to yield 3-ethyl-7-hydroxy-phthalide, IR spectrum ($CHCl_3$): C=O 1738 $cm^{-1}$.

EXAMPLE 104

7-hydroxy,3-isopropyl-phthalide (i) A solution of 8.0 g of 1-(2,2-dimethylpropanoyloxy)-3,5-dioxo-exo-10-oxatricyclo[5.2.1.0(2,6)]dec-8-ene in 25 ml of tetrahydrofuran is added dropwise to a Grignard solution of 6.8 g of isopropylmagnesium chloride in 33 ml of tetrahydrofuran in such a manner that the temperature does not exceed −20° C. When the addition is complete, the reaction mixture is allowed to warm to room temperature and is subsequently stirred for approximately 16 hours. While cooling with ice, the pH of the mixture is then adjusted to 2 with 45 ml of 2N hydrochloric acid, and the mixture is extracted twice with 300 ml of diethyl ether. The organic phase is dried over anhydrous magnesium sulfate and concentrated by evaporation under reduced pressure, and the resulting crude product is purified by chromatography on silica gel using diethyl ether/n-hexane (3:7) to yield (3aα,4β,7β,7aα)-hexahydro-1-isopropyl-3-oxo-4,7-epoxyisobenzofuran-4-yl pivalate.

(ii) The product of the preceding reaction step is introduced into concentrated sulfuric acid and the solution is stirred at 5° C. for 20 minutes. The mixture is then poured onto ice and extracted with diethyl ether. After drying the ethereal solution and concentrating it by evaporation, 7-hydroxy-3-isopropyl-phthalide is obtained in the form of colourless crystals.

EXAMPLE 105

3,7-dihydroxyphthalide 4.4 g of 3-hydroxy-7-methoxy-phthalide [see B. L. Chenard et al., J. Org. Chem. 49, 318 (1984) for its preparation] are heated at reflux temperature for 75 minutes in 100 ml of 48% hydrobromic acid. The reaction mixture is then poured onto ice-water and the aqueous mixture is extracted four times with ethyl acetate. The combined organic phases are washed with sodium chloride solution, dried over anhydrous magnesium sulfate and concentrated under reduced pressure. The crude product is filtered through a short column of silica gel using ethyl acetate as eluant and the brown oil so obtained is decolorised by heating in the presence of activated carbon to yield 2.5 g of a yellowish, amorphous solid, that is to say the crude 3,7-dihydroxyphthalide, which may possibly be used in unpurified form for the preparation of a further starting material of formula II, for example 7-hydroxy-3-methoxy-phthalide (see Example 118).

EXAMPLE 106

3,7-dihydroxyphthalide

The title compound can also be prepared as follows:
3.0 g of 3-hydroxy-7-methoxy-phthalide [see B. L. Chenard et al., J. Org. Chem. 49, 318 (1984)] are introduced in portions into a suspension of 8.2 g of aluminium trichloride in 50 ml of methylene chloride, the internal temperature being maintained at 27° C. The mixture is stirred at room temperature for a further 5 hours, is then poured into 200 ml of ice-cold 1N hydrochloric acid and extracted three times with 200 ml of ethyl acetate each time. The organic solution is washed with sodium chloride solution and dried over anhydrous magnesium sulfate. Evaporation of the solvent and recrystallisation from ethyl acetate and n-hexane yield pure 3,7-dihydroxyphthalide, m.p. 124°-126° C.

EXAMPLE 107

3,3-diisopropyl-7-hydroxy-phthalide

Analogously to the process described in Example 102, there is obtained from 1-(2,2-dimethylpropanoyloxy)-3,5-dioxo-exo-10-oxatricyclo[5.2.1.0(2,6)]dec-8-ene and isopropylmagnesium iodide, via (3aα,4β,7β,7aα)- hexahydro-1,1-diisopropyl-3-oxo-4,7-epoxyisobenzofuran-4-yl pivalate, 3,3-diisopropyl-7-hydroxy-phthalide.

EXAMPLES 108-117

Analogously to the process described in Example 103, there are obtained from 2-methoxy-N,N-diethylbenzamide, butyllithium and the appropriate aldehyde or ketone $R^{3''}R^4CO$ (see Reaction Scheme 2) the starting materials indicated in the following Table 6 of the formula IIh' or Ili'':

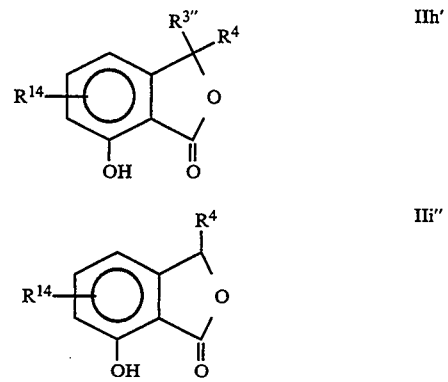

TABLE 6

| Example | formula IIh' or Ili'' | $R^{3''}$ | $R^4$ | $R^{14}$ | physical data |
|---|---|---|---|---|---|
| 108 | IIh' | tert. butyl | H | H | |
| 109 | IIh' | ethyl | methyl | H | liquid |
| 110 | IIh' | phenyl | H | H | m.p. 166-167° C. |
| 111 | Ili'' | — | methyl | H | m.p. 107-108° C. |
| 112 | Ili'' | — | H | H | solid |
| 113 | Ili'' | — | methyl | 6-methyl | m.p. 44-45° C. |
| 114 | Ili'' | — | methyl | 4-chloro | m.p. 114-115° C. |
| 115 | Ili'' | — | methyl | 4-bromo | m.p. 105-107° C. |
| 116 | Ili'' | — | n-propyl | H | $^1$H-NMR (CDCl$_3$): 5.50 ppm (double-d, 8 × 4 Hz, 1H) |
| 117 | Ili'' | — | n-butyl | H | $^1$H-NMR (CDCl$_3$): 5.50 ppm (double-d, 8 × Hz, 1H) |

EXAMPLE 118

7-hydroxy-3-methoxy-phthalide 4 drops of concentrated sulfuric acid are added to a solution of 2.5 g of 3,7-dihydroxyphthalide (in the form of the crude product—see Examples 105 and 106) in 70 ml of methanol and, after the subsequent addition of 3 Å molecular sieve, the mixture is left to stand for approximately 16 hours. The mixture is then filtered and the filtrate is concentrated by evaporation. The crude product, 3 g of yellow oil, is purified by chromatography (flash-chromatography) on silica gel using ethyl acetate/n-hexane (3:7) to yield 1.9 g (70% of the theoretical yield) of 7-hydroxy-3-methoxy-phthalide in the form of reddish crystals, m.p. 77°-79° C. (after crystallisation from diethyl ether/n-hexane); IR spectrum (CHCl$_3$): C=O 1745 cm$^{-1}$.

EXAMPLES 119-129

Analogously to the process described in Example 118, there are obtained from 3,7-dihydroxy-phthalide or 3,7-dihydroxy-3-methyl-phthalide and the relevant hydroxy compound in the presence of a catalytic amount of sulfuric acid the starting materials indicated in the following Table 7 of the formula IIc' or IIf':

[Structures of IIc' and IIf' with OH and R3', R4' substituents]

| Example | formula IIc' or IIf' | R3' | R4' | physical data |
|---|---|---|---|---|
| 119 | IIf' | isopropoxy | — | m.p. 98–100° C. |
| 120 | IIf' | benzyloxy | — | m.p. 94–95° C. |
| 121 | IIf' | tert.butoxy | — | m.p. 144–146° C. |
| 122 | IIf' | ethoxy | — | $^1$H-NMR (CDCl$_3$): 6.39 ppm(s, 1H) |
| 123 | IIc' | methoxy | methyl | IR spectrum (CHCl$_3$): C=O 1738 cm$^{-1}$ |
| 124 | IIc' | 2-chloroethoxy | H | m.p. 117–119° C. |
| 125 | IIc' | propargyloxy | H | m.p. 94–96° C. |
| 126 | IIc' | n-propoxy | H | m.p. 63–64° C. |
| 127 | IIc' | 2-methoxy-ethoxy | H | m.p. 79–80° C. |
| 128 | IIc' | 2-methylthio-ethoxy | H | |
| 129 | IIc' | n-butoxy | H | |

EXAMPLE 130

7-hydroxy-3-methoxy-3-methyl-phthalide

The title compound (see also Example 123) can also be prepared as follows:

1.5 g of 3-hydroxy-7-methoxy-3-methyl-phthalide (see the following Example 131) are left to stand at room temperature for one hour in 50 ml of methanol saturated with hydrogen chloride, and the mixture is then taken up in ethyl acetate and washed with ice-cold sodium chloride solution. After removal of the solvent, 3,7-dimethoxy-3-methyl-phthalide, m.p. 101°–104° C., is obtained.

1.45 g of the above product are stirred in 20 ml of methylene chloride with 3.4 g of aluminium trichloride for 45 minutes, ice-water is then added to the mixture and it is extracted twice with methylene chloride. The organic phase is dried over anhydrous magnesium sulfate and concentrated under reduced pressure to yield 7-hydroxy-3-methoxy-3-methyl-phthalide, m.p. 106°–109° C.; IR spectrum (CHCl$_3$): C=O 1740 cm$^{-1}$.

EXAMPLE 131

3,7-dihydroxy-7-methoxy-3-methyl-phthalide 5.4 g of 3-methoxy-phthalic acid anhydride [see A. V. R. Rao et al., Indian J. Chew. 20B, 248 ff. (1981)], 4.7 g of malonic acid and 9 ml of triethylamine are heated slowly. The suspension becomes stirrable at 55° C. and, from 68° C., moderately vigorous CO$_2$ evolution occurs. The internal temperature is maintained at 73° C. until gas evolution ceases (about 1 hour) and the reaction mixture is then heated at reflux temperature (internal temperature 85° C.) for a further 4 hours. When it has cooled, the reaction mixture is treated with water and extracted with ethyl acetate. The aqueous phase is then adjusted to pH 1.7 and extracted three times with fresh ethyl acetate, dried over anhydrous sodium sulfate and concentrated by evaporation under reduced pressure. Fractional crystallisation (ethyl acetate/n-hexane) yields 3-hydroxy-7-methoxy-3-methyl-phthalide, m.p. 156°–158° C.; IR spectrum (CHCl$_3$): C=O 1772 cm$^{-1}$.

1.9 g of the above product are dissolved in 20 ml of methylene chloride, and the solution is treated at −70° C. with 3.5 g of boron tribromide. The mixture is then taken up in ice-cold dilute hydrochloric acid and the organic phase is extracted with ethyl acetate, dried over anhydrous sodium sulfate and concentrated by evaporation under reduced pressure to yield crude 3,7-dihydroxy-3-methyl-phthalide in the form of an amorphous solid which may possibly be used in unpurified form for the preparation of a further starting material of formula II (for example 7-hydroxy-3-methoxy-3-methyl-phthalide).

EXAMPLE 132

4-hydroxy-1,3-dihydro-3-oxo-(-isobenzofuran-carboxamide 2.8 g of 3,7-dihydroxy-phthalide (see Examples 105 and 106) are introduced into a solution of 7.5 g of potassium cyanide in 35 ml of water, and 25 ml of concentrated hydrochloric acid are slowly added to the mixture while cooling with ice, so that the internal temperature does not exceed 10° C. The reaction mixture is maintained at room temperature for a further 5 hours and then the crystals are filtered off. Having been washed with water and dried well, the product (m.p. 213°–215° C.) is pure 4-hydroxy-1,3-dihydro-3-oxo-1-isobenzofurancarboxamide.

EXAMPLE 133

7-hydroxy-3-trifluoromethyl-phthalide

A mixture of 26.4 g of N,N-dimethyl-2-methoxy-benzamide and 19 ml of tetramethylethylenediamine in 120 ml of absolute tetrahydrofuran is treated at −70° C. with 100 ml of a 1.4-molar solution of sec-butyllithium in cyclohexane/isooctane and, after 45 minutes, 27.3 ml of trifluoroacetoacetic ester are added dropwise within 20 minutes. The mixture is allowed to warm to room temperature for approximately 16 hours, 200 ml of water are added and the mixture is acidified to pH 2 with hydrochloric acid. The mixture is extracted with a total of 600 ml of diethyl ether, and the organic phase is dried over anhydrous magnesium sulfate and concentrated by evaporation under reduced pressure. The residue is chromatographed on silica gel (eluant: ethyl acetate/n-hexane 1:1) to yield 3-hydroxy-7-methoxy-3-trifluoromethyl-phthalide, IR spectrum (CHCl$_3$): C=O 1785 cm$^{-1}$.

1.5 g of sodium borohydride are added in portions at room temperature to 11.1 g of the above product in 140 ml of ethanol. The mixture is taken up in hydrochloric acid/ice water and extracted with fresh diethyl ether. Removal of the solvents and subsequent chromatography yield pure 7-methoxy-3-trifluoromethyl-phthalide, IR spectrum (CHCl$_3$): C=O 1785 cm$^{-1}$.

4.6 g of the above product are treated dropwise at −70° C. in 30 ml of tetrahydrofuran with 7.0 g of boron tribromide. The mixture is allowed to warm slowly to room temperature and is then treated with ice-water and extracted by shaking with ethyl acetate. The solvents are removed and the crude product is filtered over silica gel (eluant: ethyl acetate/n-hexane 1:1) to yield crystalline 7-hydroxy-3-trifluoromethyl-phthalide, IR spectrum (CHCl$_3$): C=O 1766 cm$^{-1}$; $^1$H-NMR (CDCl$_3$): 5.68 ppm (q, 6 Hz, 1H).

EXAMPLE 134

3.7-dihydroxy-3-trifluoromethyl-phthalide

The title compound can be prepared analogously to the above Example (133) from 3-hydroxy-7-methoxy-3-trifluoromethyl-phthalide (see Example 133) and boron tribromide; m.p. 128°-1290° C.

EXAMPLE 135

7-mercapto-3-methyl-phthalide 24 g of 7-hydroxy-3-methylphthalide are introduced into an aqueous solution of 8.2 g of potassium hydroxide in 130 ml of water, and the mixture is then treated dropwise, while stirring well and cooling, with 23.5 g of dimethylcarbamoyl chloride. After 90 minutes, the mixture is adjusted to pH 11 with sodium hydroxide solution, ice is added and the mixture is extracted twice with ethyl acetate. Drying and evaporation of the solvent and also recrystallisation from ethyl acetate and n-hexane yield O-(1,3-dihydro-3-methyl-1-oxo-7-isobenzofuranyl)-dimethylthiocarbamate, m.p. 163°-164° C.

26 g of the above product are taken up in 180 ml of resorcinol dimethyl ether, and the mixture is heated at 212° C for 24 hours. When it has cooled, the reaction mixture is filtered through silica gel using ethyl acetate/n-hexane (2:1) as eluant and, after removal of the solvents, is recrystallised to yield S-(1,3-dihydro-3-methyl-1-oxo-7-isobenzofuranyl)-dimethylthiocarbamate, m.p. 144°-145° C.

18.4 g of the above product in a mixture of 120 ml of methanol and 60 ml of chloroform is treated with a solution of 4.2 g of sodium in 180 ml of methanol. The mixture is stirred at room temperature for approximately 3 hours and then 390 ml of ethyl acetate are added. The solvents are then removed for the most part under reduced pressure, and the residue is treated with saturated sodium chloride solution and extracted by shaking with ethyl acetate. Filtration on silica gel (eluant: ethyl acetate/n-hexane 1:2) yields pure 7-mercapto-3-methyl-phthalide, m.p. 40° C.

EXAMPLE 136

7-hydroxy-3-methyl-isobenzofuran-1(3H)-thione 3.9 g of 7-hydroxy-3-methyl-phthalide (see Examples 101 and 111) and 5.1 g of Lawesson reagent are heated in 20 ml of xylene for 4 hours at 140° C. Chromatographic filtration of the mixture on silica gel [eluant: ethyl acetate/n-hexane (1:9)] yields 7-hydroxy-3-methyl-isobenzofuran-1(3H)-thione, m.p. 39°-41° C.; IR spectrum (CHCl$_3$): C=O 1624, 1604, 1368, 1330, 1304, 1165 cm$^{-1}$; mass spectrum: 180 (M+=100), 165(58), 137(24).

EXAMPLE 137

7-hydroxy-3-vinyl-phthalide 600 mg of 3,7-dihydroxyphthalide (see Examples 105 and 106) are stirred in 20 ml of absolute tetrahydrofuran at −78° C. Under an argon atmosphere, 6 ml of a 2M vinyl-magnesium chloride solution in tetrahydrofuran are then added by means of a syringe. The reaction mixture is allowed to warm to room temperature and is poured onto 100 ml of 1N hydrochloric acid. It is then extracted twice with 75 ml of ethyl acetate each time and the combined organic phases are washed with sodium chloride solution and dried with anhydrous magnesium sulfate, and the organic solution is concentrated under reduced pressure. 600 mg of crude product remain which are subjected to flash-chromatography on silica gel using ethyl acetate/n-hexane (1:1).

In this manner, 380 mg (60% of the theoretical yield) of 7-hydroxy-3-vinyl-phthalide are obtained.

EXAMPLE 138

7-hydroxy-3-isopropylidene-phthalide (i) Analogously to the process described in Example 104, 10 g of 1-(2,2-dimethylpropanoyloxy)-3,5-dioxo-exo-10-oxatricyclo[5.2.1.0(2,6)]dec-8-ene are introduced into 25 ml of tetrahydrofuran at −35° C., and 3.9 g of isopropylmagnesium chloride in 30 ml of tetrahydrofuran are then added to the solution. The mixture is allowed to warm to room temperature, then 27 ml of 2N hydrochloric acid are added, the whole is extracted twice with diethyl ether, and the organic phase is dried over anhydrous magnesium sulfate and concentrated by evaporation to yield (3a$\alpha$,4$\beta$,7$\beta$,7a$\alpha$)-hexahydro-1-hydroxy-1-isopropyl-3-oxo-4,7-epoxyisobenzofuran-4-yl pivalate in the form of the crude product.

(ii) The crude product so obtained is taken up in concentrated sulfuric acid at 0° C. and the solution is stirred for 20 minutes. The solution is then poured onto ice, the aqueous mixture is extracted with diethyl ether and the organic phase is dried over anhydrous magnesium sulfate. The oily crude product is then separated by chromatography using a 20% solution of diethyl ether in n-hexane to yield 7-hydroxy-3-isopropylidene-phthalide in the form of a solid which is not further characterised.

EXAMPLE 139

(Z)-3-ethylidene-7-hydroxy-phthalide 14.5 ml of dimethyl phosphite are added dropwise at from 0° to 10° C. under nitrogen to a solution of 3.6 g of sodium in 130 ml of methanol and, simultaneously, 20 g of 3-hydroxy-7-methoxy-phthalide (see Example 118) are introduced in portions. The mixture is subsequently stirred at room temperature for 30 minutes and then 11.3 ml of methanesulfonic acid are added within 10 minutes. After a further hour, most of the methanol is distilled off under reduced pressure, the residue is poured onto 400 ml of dilute hydrochloric acid and ice and the aqueous mixture is extracted three times with 900 ml of ethyl acetate. The organic phase is washed with sodium chloride solution, dried over anhydrous magnesium sulfate and concentrated by evaporation under reduced pressure, and the residue is recrystallised from ethyl acetate/n-hexane to yield pure 3-dimethoxyphosphonyl-7-methoxy-phthalide, m.p. 129°-131° C.

12.3 g of the above product are dissolved in 750 ml of dry tetrahydrofuran, and the solution is treated at 3° C. with 5.2 g of potassium tert-butanolate. After subsequently stirring at that temperature for one hour, 2.8 ml of acetaldehyde are added dropwise and the reaction mixture is then stirred at 12° C. for a further hour. It is poured onto dilute hydrochloric acid and ice as described above and extracted with ethyl acetate, and the organic phase is washed with water and with sodium chloride solution, dried over anhydrous magnesium sulfate and concentrated by evaporation under reduced pressure. The residue is filtered through silica gel [eluant: ethyl acetate/n-hexane (7:3)] to yield crude 7-methoxy-3-ethyl-idene-phthalide in the form of an (E/Z) mixture, $^1$H-NMR (CDCl$_3$): 5.88 ppm and 5.64 ppm (2q, J=7.5 Hz, (E) and (Z) C$\underline{H}$=). A first fraction contains pure (Z)-7-methoxy-3-ethylidene-phthalide, m.p. 106°–109° C.

1.1 g of the above product are stirred together with 2.8 g of aluminium trichloride in 50 ml of methylene chloride at room temperature for 2 hours, and the mixture is then poured onto ice-cold dilute hydrochloric acid and extracted with methylene chloride. The organic phase is washed with semi-saturated sodium chloride solution, dried over anhydrous magnesium sulfate and concentrated under reduced pressure to yield pure (Z)-3-ethylidene-7-hydroxy-phthalide, $^1$H-NMR (CDCl$_3$): 5 70 ppm (q, J=7, 5 Hz, C$\underline{H}$=).

EXAMPLES 140–144

Analogously to the process described in Example 139, the starting materials indicated in the following Table 8, of the formula

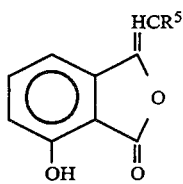

IIk' are obtained from 3-hydroxy-7-methoxy-phthalide via 3-dimethoxyphosphonyl-7-methoxy-phthalide which is reacted with the appropriate aldehyde to give the corresponding compound XIX which in turn is treated with aluminium trichloride (see Reaction Scheme 3: XVII→XVIII→XIX→IIk).

| Example | R$^5$ | physical data |
|---|---|---|
| 140 | ethyl | $^1$H-NMR (CDCl$_3$): 5.89 and 5.66 ppm [2q, J=8Hz, (E) and (Z) |
| 141 | 4-methoxy-phenyl | $^1$H-NMR (CDCl$_3$): 6.40 ppm (s, CH=) |
| 142 | phenyl | $^1$H-NMR (CDCl$_3$): 6.45 ppm (s, CH=) |
| 143 | 3-methoxy-phenyl | $^1$H-NMR (CDCl$_3$): 6.43 ppm (s, CH=) |
| 144 | n-propyl | $^1$H-NMR (CDCl$_3$): 5.90 und 5.67 ppm [2q, J=8Hz, (E) and (Z) CH=] |

EXAMPLE 145

3,4-dihydro-8-hydroxy-4-methyl-1H-2-benzopyran-1-one 39.5 g of N,N-dimethyl-2-methoxy-benzamide and 28.5 ml of tetramethylethylenediamine are introduced into 190 ml of absolute tetrahydrofuran and the mixture is lithiated at −70° C. with 150 ml of a 1.4-molar sec-butyllithium solution in cyclohexane/isopentane. After subsequently stirring at −70° C. for 45 minutes, 25.6 ml of ethyl bromide are added dropwise within 25 minutes and the reaction mixture is then allowed to warm slowly to room temperature. Water is then added and the mixture is adjusted to pH 2 with hydrochloric acid and extracted twice with diethyl ether. The residue is purified on silica gel using ethyl acetate/n-hexane (4:6) to yield 6-ethyl-N,N-dimethyl-2-methoxy-benzamide in the form of a colourless oil, $^1$H-NMR (CDCl$_3$): 3 82 ppm (m), 3.40 ppm (m) and 3.12 ppm (2q, N(C$\underline{H_2}$CH$_3$)$_2$), 2.56 ppm (m, C$\underline{H_2}$CH$_3$).

5.8 g of the above product and 3.5 g of tetramethylethylenediamine are lithiated at −70° C. in 150 ml of absolute tetrahydrofuran with 24.8 ml of 1.4-molar sec-butyllithium solution in cyclohexane/isooctane and, after 1 hour, 3 g of freshly sublimed formaldehyde are added. The mixture is allowed to warm slowly to room temperature, 30 ml of concentrated hydrochloric acid are added (pH 1.5) and the mixture is extracted twice with ethyl acetate. The solvents are then removed under reduced pressure. The oily product which remains is taken up in 150 ml of 48% hydrobromic acid and the mixture is heated at reflux temperature for 6 hours. It is extracted with fresh ethyl acetate, washed with dilute sodium bicarbonate solution, dried over anhydrous magnesium sulfate and concentrated by evaporation under reduced pressure. The product which remains is chromatographed (eluant: ethyl acetate/n-hexane 1:3) to yield 3,4-dihydro-8-hydroxy-4-methyl-1H-2-benzopyran-1-one in the form of a yellow oil, $^1$H-NMR (CDCl$_3$): 4.56 and 4.27 ppm (2q, 7×11 Hz, 2H), 3.14 ppm (m, 1H), 1.36 ppm (d, 7 Hz, CH$_3$).

EXAMPLE 146 cis- and trans-3,4-dihydro-8-hydroxy-3,4-dimethyl-1H-2-benzopyran-1-one

Analogously to the process described in Example 143, there can be prepared from 6-ethyl-N,N-dimethyl-2-methoxy-benzamide and acetaldehyde 3,4-trans- and cis-3,4-dihydro-8-hydroxy-3,4-dimethyl-1H-2-benzopyran-1-one, IR spectrum (CHCl$_3$): 1675 cm$^{-1}$, which is used for the preparation of the compounds of Examples 79 and 80.

EXAMPLE 147

7-hydroxy-3-methyl-isobenzofuran-1(3H)-thione 1.67 g of 7-hydroxy-3-methyl-phthalide (see Example 101) and 2.17 g of 2,4-bis(4-methoxyphenyl)-2,4-dithioxo-1,3,2,4-dithiadiphosphetan (Lawesson reagent) are heated in 8 ml of xylene at 138° C. for 3 hours. When it has cooled, the reaction material is filtered directly over a column of silica gel [eluant: ethyl acetate/n-hexane (1:4)] in order to isolate the 7-hydroxy-3-methyl-isobenzofuran-1(3H)-thione; m.p. 38°–40° C.; IR spectrum: 1624, 1604, 1368, 1330, 1304, 1165 cm$^{-1}$; mass spectrum: 180 (M$^+$=100), 165 (58), 137 (24).

III. FORMULATION EXAMPLES

EXAMPLE 148

To prepare a 25% wettable powder, the constituents listed below are mixed with one another:

| | % by weight |
|---|---|
| compound (active ingredient) according to the invention | 25 |
| hydrated silicic acid (carrier, grinding adjuvant) | 20 |
| sodium lauryl sulfate (wetting agent) | 2 |
| sodium lignosulfonate (dispersant) | 4 |
| kaolin (carrier) | 49 |
| | 100 |

First of all, the liquid or melted active ingredient is applied in a grinding apparatus to the previously introduced silicic acid. The further constituents are then mixed in and the mixture is finely ground using a pinned disk mill or a comparable grinding apparatus.

When stirred into water, the resulting wettable powder produces a fine suspension which is suitable as a ready-for-use spray liquor.

Compounds according to the invention that are liquid or have a low melting point, that is to say up to approximately 100° C., are especially suitable as active ingredients in this formulation.

EXAMPLE 149

Compounds according to the invention having high melting points, that is to say approximately 100° C. and higher, can preferably be used as active ingredients in more concentrated wettable powders, for example as follows:

| | % by weight |
|---|---|
| compound (active ingredient) according to the invention | 75 |
| hydrated silicic acid (carrier, grinding adjuvant) | 1 |
| alkylnaphthalenesulfonate and alkylcarboxylate sulfate in the form of sodium salts, e.g. Morwett ® EFW (De Soto) [wetting agent] | 2 |
| sulfoanted naphthalene-formaldehyde condensate, in the form of the sodium salt, e.g. Morwett ® D-425 (De Soto) [dispersant] | 10 |
| polyvinylpyrrolidone, e.g. PVP-K-30 (GAF Corp.) [binder] | 1 |
| kaolin (carrier) | 11 |

The constituents are mixed with one another and finely ground using a pinned disk mill or a comparable grinding apparatus, especially a jet mill. When stirred into water, the resulting wettable powder produces a fine suspension of any desired concentration, which is suitable as a ready-for-use spray liquor.

EXAMPLE 150

A wettable powder based on the above Formulation Example (149) can also be converted into dispersible granules. For that purpose, the ground powder is sprayed with an aqueous solution of the binder in a suitable granulating apparatus (e.g. granulating plate, mixing drum, intensive mixer or fluidized-bed granulator) until agglomerates have formed. The water added is then removed again in a drying process and the granules of the desired size are screened out. The resulting granules have various advantages over the wettable powder (no dust formation when being applied, ability to be measured out more easily owing to better flowing properties). Application is effected after stirring the preparation into water and after complete disintegration of the granules into the primary particles in exactly the same manner as with the wettable powder.

EXAMPLE 151

The compounds according to the invention have limited solubility in customary organic solvents. Accordingly, only emulsifiable concentrates of relatively low concentration are possible; for example:

| | |
|---|---|
| compound (active ingredient) according to the invention | 125 g/l |
| Soprophor ® BSU (emulsifier, Rhône-Poulenc) | 300 g/l |
| N-methyl-2-pyrrolidone (solvent) | to 1000 ml |

The active ingredient and the emulsifier are introduced into the solvent with stirring and the mixture is stirred until a homogeneous solution is produced.

The resulting emulsifiable concentrate can be emulsified in water and in that manner produces a ready-for-use spray liquor of the desired concentration.

EXAMPLE 152

Compounds according to the invention having a melting point of approximately 60° C. and higher can also be formulated as so-called "flowables", for example:

| | |
|---|---|
| compound (active ingredient) according to the invention | 250 g/l |
| ethylene glycol (anti-freeze) | 80 g/l |
| silicic acid (anti-settling agent) | 5 g/l |
| xanthan gum, e.g. Kelzan ® (Kelco) [thickener] | 2 g/l |
| silicone antifoam, e.g. Rhodorsil ® 426 (Rhône-Poulenc) | 5 g/l |
| nonylphenol polyethoxylate (wetting agent) | 20 g/l |
| sulfonated naphthalene-formaldehyde condensate in the form of the sodium salt, e.g. Morwett ® D-425 (De Soto) (dispersant) | 40 g/l |
| water | to 1000 ml |

The formulation adjuvants are dissolved in water. The pre-ground active ingredient is dispersed in the solution with stirring. The resulting coarse suspension is then subjected to wet-grinding (e.g. in a colloid mill, agitator ball mill). If desired, it is then possible to add further substances in small amounts, such as anti-foams, anti-settling agents and biocides.

For application, the resulting "flowable" can be diluted with water as desired and in that manner produces a ready-for-use spray liquor of the desired concentration.

We claim:

1. A compound of the formula

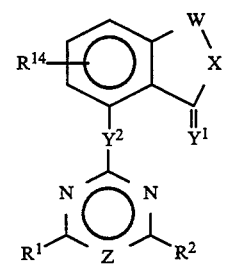

I wherein

W is one of the divalent groups a)–d)

a)

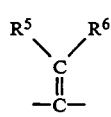

b)

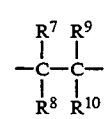

c)

-continued

  d)

X, $Y^1$ and $Y^2$ are each oxygen or sulfur,
Z is $CR^{13}$,
$R^1$ is hydrogen, fluorine, chlorine, $C_{1-3}$alkyl, halomethyl, methoxymethyl, $C_{1-3}$alkoxy, difluoromethoxy or methylthio,
$R^2$ is methyl, $C_{1-2}$alkoxy, $C_{1-2}$fluoroalkoxy, $C_{1-2}$alkylamino, di($C_{1-2}$alkyl)amino or N-methoxymethylamino,
$R^3$ is hydrogen, fluorine, chlorine, bromine, $C_{1-6}$alkyl or $C_{1-6}$alkyl substituted by halogen or nitro, $C_{2-3}$alkenyl, $C_{2-3}$alkynyl, phenyl, hydroxy, $C_{1-6}$alkoxy or $C_{1-6}$alkoxy substituted by halogen, $C_1$-$C_2$-alkylthio, N-($C_1$-$C_2$-alkyl)-carbamoyl, or $C_1$-$C_2$-alkoxy, $C_{1-6}$alkylthio, phenoxy, phenylthio, cyano, thiocyano, formyl, carboxy, $C_{2-5}$alkoxycarbonyl, carbamoyl, formyloxy, $C_{2-5}$alkanoyloxy, $C_{2-5}$alkoxycarbonyloxy, $C_{2-3}$alkylcarbamoyloxy, di($C_{1-2}$alkyl)-carbamoyloxy or di($C_{1-2}$alkoxy)phosphonyl,
$R^4$ is hydrogen, $C_{1-6}$alkyl or trifluoromethyl,
$R^5$ is hydrogen, $C_{1-6}$alkyl, phenyl or phenyl substituted by methoxy,
$R^6$ is hydrogen or methyl,
$R^7$, $R^8$ and $R^9$ each independently of the others is hydrogen or $C_{1-3}$alkyl,
$R^{10}$ is hydrogen or $C_{1-3}$alkoxy,
$R^{11}$ and $R^{12}$, each independently of the other, is hydrogen or $C_{1-3}$alkyl,
$R^{13}$ is hydrogen, fluorine, chlorine or methyl and
$R^{14}$ is hydrogen, halogen, $C_{1-2}$alkyl or $C_{1-2}$alkoxy.

2. A compound according to claim 1, wherein W is a group a) and $R^3$ is hydrogen, fluorine, chlorine, bromine, unsubstituted or substituted $C_{1-6}$alkyl, $C_{2-3}$alkenyl, $C_{2-3}$alkynyl, unsubstituted or substituted phenyl, hydroxy, $C_{1-6}$alkoxy, $C_{1-6}$alkylthio, phenoxy, phenylthio, cyano or $C_{2-5}$alkoxycarbonyl and $R^4$ is hydrogen or $C_{1-6}$alkyl, or $R^3$ is hydrogen, fluorine, chlorine, bromine, $C_{1-6}$alkyl, hydroxy, $C_{1-6}$alkoxy, $C_{1-6}$alkylthio, phenoxy, phenylthio or cyano and $R^4$ is trifluoromethyl; or W is a group b), c) or d) wherein $R^5$, $R^6$, $R^7$, $R^8$, $R^9$, R10, $R^{11}$ and $R^{12}$ are as defined in claim 1; and X is oxygen, $Y^1$, $Y^2$ and Z are as defined in claim 1 and $R^1$ is fluorine, chlorine, $C_{1-3}$alkyl, fluoromethyl, methoxymethyl, $C_{1-3}$alkoxy, difluoromethoxy or methylthio, $R^2$ is methyl, $C_{1-2}$alkoxy or $C_{1-2}$fluoroalkoxy, and $R^{14}$ is hydrogen.

3. A compound according to claim 1, wherein W is a group a) wherein $R^3$ is hydrogen, vinyl, ethynyl, hydroxy, $C_{1-4}$alkoxy, $C_{1-2}$alkoxy that is substituted by halogen, vinyl, ethynyl, $C_{1-2}$alkoxy, cyano, carboxymethyl or by $C_{2-3}$alkoxycarbonylmethyl, $C_{1-2}$alkylthio, cyano, carboxy, $C_{2-3}$alkoxycarbonyl or carbamoyl and $R^4$ is hydrogen or $C_{1-4}$alkyl.

4. A compound according to claim 1, wherein W is a group b) wherein $R^5$ is hydrogen or $C_{1-3}$alkyl and $R^6$ is hydrogen.

5. A compound according to claim 1, wherein W is a group c) wherein $R^7$ $R^8$ and $R^9$ are each hydrogen or methyl.

6. A compound according to claim 1, wherein W is a group d) wherein $R^{11}$ and $R^{12}$ are each hydrogen or methyl.

7. A compound according to claim 1, wherein X and $Y^1$ are each oxygen.

8. A compound according to claim 1, wherein $Y^2$ is oxygen.

9. A compound according to claim 1, wherein Z is CH.

10. A compound according to claim 1, wherein $R^1$ is hydrogen, chlorine, methyl, methoxy or difluoromethoxy and $R^2$ is methoxy, ethoxy, methylamino, dimethylamino or N-methoxymethylamino.

11. A compound according to claim 1, wherein at least one of $R^1$ and $R^2$ is methoxy.

12. A compound according to claim 1, wherein $R^{14}$ is hydrogen.

13. A compound according to claim 1, selected from the group consisting of:
7-[(4,6-dimethoxy-pyrimidin-2-yl)oxy]-3-methyl-phthalide,
7-[(4,6-dimethoxy-pyrimidin-2-yl)oxy]-phthalide,
3-ethyl-7-[(4,6-dimethoxy-pyrimidin-2-yl)oxy]-phthalide,
7-[(4,6-dimethoxy-pyrimidin-2-yl)oxy]-3-isopropyl-phthalide,
7-[(4,6-dimethoxy-pyrimidin-2-yl)oxy]-3-methoxy-phthalide,
7-[(4-methoxy-6-methyl-pyrimidin-2-yl)oxy]-3-methyl-phthalide,
(Z)-3-ethylidene-7-[(4,6-dimethoxy-pyrimidin-2-yl)oxy]-phthalide,
8-[(4,6-dimethoxy-pyrimidin-2-yl)oxy]-3-methyl-isochroman-1-one,
7-[(4,6-dimethoxy-pyrimidin-2-yl)thio]-3-methyl-phthalide,
3-ethoxy-7-[(4,6-dimethoxy-pyrimidin-2-yl)oxy]-phthalide,
7-[(4,6-dimethoxy-pyrimidin-2-yl)oxy]-3-methoxy-3-methyl-phthalide,
7-[(4-chloro-6-methoxy-pyrimidin-2-yl)oxy]-3-methyl-phthalide,
7-[(4-ethoxy-6-methoxy-pyrimidin-2-yl)oxy]-3-methyl-phthalide,
8-[(4,6-dimethoxy-pyrimidin-2-yl)oxy]-3,4-dimethyl-isochroman-2-one,
7-[(4,6-dimethoxy-pyrimidin-2-yl)oxy]-3-methylthio-phthalide,
7-[(4,6-dimethoxy-pyrimidin-2-yl)oxy]-3-vinyl-phthalide and
3-cyano-7-[(4,6-dimethoxy-pyrimidin-2-yl)oxy]-phthalide.

14. A compound according to claim 1, selected from the group consisting of:
7-[(4,6-dimethoxy-pyrimidin-2-yl)oxy]-3,6-dimethyl-phthalide,
3-carbamoyl-7-[(4,6-dimethoxy-pyrimidin-2-yl)oxy]-phthalide,
3-(2-chloroethoxy)-7-[(4,6-dimethoxy-Pyrimidin-2-yl)oxy]-phthalide,
7-[(4,6-dimethoxy-pyrimidin-2-yl)oxy]-3-propargyloxy-phthalide,
7-[(4,6-dimethoxy-pyrimidin-2-yl)oxy]-3-(n-propoxy)-phthalide,
7-[(4,6-dimethoxy-pyrimidin-2-yl)oxy]-3-(2-methoxyethoxy)-phthalide,
7-[(4-methoxy-pyrimidin-2-yl)oxy]-3-methyl-phthalide,
7-[(4-chloro-6-methoxy-pyrimidin-2-yl)oxy]-3-methoxy-phthalide, 7-[(4,6-dimethoxy-pyrimidin-2-yl)oxy]-3-hydroxy-phthalide, 3-cyanomethoxy-7-[(4,6-dimethoxy-pyrimidin-2-yl)oxy]-phthalide, 7-[(4,6-dimethoxy-pyrimidin-2-yl)oxy]-3-(methoxycarbonyl-methoxy)-phthalide, 3-ethoxycarbonylmethyl-7-[(4,6-dimethoxy-Pyrimidin-2-yl)oxy]-phthalide, 7-[(4,6-dimethoxy-pyrimidin-2-yl)oxy]-3-methyl-2-benzothiophen-1(3H)-one and 7-[(4,6-dimethoxy-pyrimidin-2-yl)oxy]-3-methyl-isobenzofuran-1(3H)-thione.

15. The compound 7-[(4,6-dimethoxy-pyrimidin-2-yl)oxy]-3-methoxy-phthalide according to claim 1.

16. A weed control composition and plant-growth-regulating composition which comprises an effective mount of at least one compound of the formula

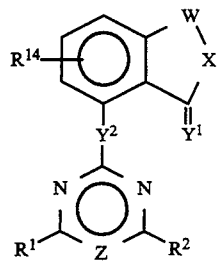

wherein

W is one of the divalent groups a)–d)

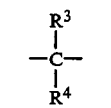 a)

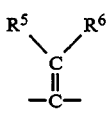 b)

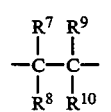 c)

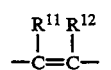 d)

X, $Y^1$ and $Y^2$ are each oxygen or sulfur,

Z is $CR^{13}$, $R^1$ is hydrogen, fluorine, chlorine, $C_{1-3}$alkyl, halomethyl, methoxymethyl, $C_{1-3}$alkoxy, difluoromethoxy or methylthio, $R^2$ is methyl, $C_{1-2}$alkoxy, $C_{1-2}$fluoroalkoxy, $C_{1-2}$alkylamino, di($C_{1-2}$alkyl)amino or N-methoxymethylamino, $R^3$ is hydrogen, fluorine, chlorine, bromine, $C_{1-6}$alkyl or $C_{1-6}$alkyl substituted by halogen or nitro, $C_{2-3}$alkenyl, $C_{2-3}$alkynyl, phenyl, hydroxy, $C_{1-6}$alkoxy or $C_{1-6}$alkoxy substituted by halogen, $C_1$-$C_2$-aralkylthio, N-($C_1$-$C_2$-alkyl)-carbamoyl, or $C_1$-$C_2$-alkoxy, $C_{1-6}$alkylthio, phenoxy, phenylthio, cyano, thiocyano, formyl, carboxy, $C_{2-5}$alkoxycarbonyl, carbamoyl, formyloxy, $C_{2-5}$alkanoyloxy, $C_{2-5}$alkoxycarbonyloxy, $C_{2-3}$alkylcarbamoyloxy, di($C_{1-2}$alkyl)-carbamoyloxy or di($C_{1-2}$alkoxy)phosphonyl, $R^4$ is hydrogen, $C_{1-6}$alkyl or trifluoromethyl, $R^5$ is hydrogen, $C_{1-6}$alkyl, phenyl or phenyl substituted by methoxy, $R^6$ is hydrogen or methyl, $R^7$, $R^8$ and $R^9$ each independently of the others is hydrogen or $C_{1-3}$alkyl, $R^{10}$ is hydrogen or $C_{1-3}$alkoxy, $R^{11}$ and $R^{12}$, each independently of the other, is hydrogen or $C_{1-3}$alkyl, $R^{13}$ is hydrogen, fluorine, chlorine or methyl and $R^{14}$ is hydrogen, halogen, $C_{1-2}$alkyl or $C_{1-2}$alkoxy.

17. A composition according to claim 16 for controlling weeds.

18. A weed control composition according to claim 17, which comprises an effective amount of at least one compound selected from the group consisting of:

7-[(4,6-dimethoxy-pyrimidin-2-yl)oxy]-3-methyl-phthalide,

7-[(4,6-dimethoxy-pyrimidin-2-yl)oxy]-phthalide, 3-ethyl-7-[(4,6-dimethoxy-pyrimidin-2-yl)oxy]-phthalide, 7-[(4,6-dimethoxy-pyrimidin-2-yl)oxy]-3-isopropyl-phthalide 7-[(4,6-dimethoxy-pyrimidin-2-yl)oxy]-3-methoxy-phthalide 7-[(4-methoxy-6-methyl-pyrimidin-2-yl)oxy]-3-methyl-phthalide, (Z)-3-ethylidene-7-[(4,6-dimethoxy-pyrimidin-2-yl)oxy]-phthalide, 8-[(4,6-dimethoxy-pyrimidin-2-yl)oxy]-3-methyl-isochroman-1-one, 7-[(4,6-dimethoxy-pyrimidin-2-yl)thio]-3-methyl-phthalide, 3-ethoxy-7-[(4,6-dimethoxy-pyrimidin-2-yl)oxy]-phthalide, 7-[(4,6-dimethoxy-pyrimidin-2-yl)oxy]-3-methoxy-3-methyl-phthalide, 7-[(4-chloro-6-methoxy-pyrimidin-2-yl)oxy]-3-methyl-phthalide, 7-[(4-ethoxy-6-methoxy-pyrimidin-2-yl)oxy]-3-methyl-phthalide, 8-[(4,6-dimethoxy-pyrimidin-2-yl)oxy]-3,4-dimethyl-isochroman-2-one, 7-[(4,6-dimethoxy-pyrimidin-2-yl)oxy]-3-methylthio-phthalide, 7-[(4,6-dimethoxy-pyrimidin-2-yl)oxy]-3-vinyl-phthalide and 3-cyano-7-[(4,6-dimethoxy-pyrimidin-2-yl)oxy]-phthalide, and formulation adjuvants.

19. A weed control composition and plant-growth-regulating composition according to claim 16, which comprises an effective amount of at least one compound selected from the group consisting of:

7-[(4,6-dimethoxy-pyrimidin-2-yl)oxy]-3,6-dimethyl-phthalide, 3-carbamoyl-7-[(4,6-dimethoxy-pyrimidin-2-yl)oxy]-phthalide, 3-(2-chloroethoxy)-7-[(4,6-dimethoxy-pyrimidin-2-yl)oxy]-phthalide, 7-[(4,6-dimethoxy-pyrimidin-2-yl)oxy]-3-propargyloxy-phthalide, 7-[(4,6-dimethoxy-pyrimidin-2-yl)oxy]-3-(n-propoxy)-phthalide, 7-[(4,6-dimethoxy-pyrimidin-2-yl)oxy]-3-(2-methoxyethoxy)-phthalide, 7-[(4-methoxy-pyrimidin-2-yl)oxy]-3-methyl-phthalide, 7-[(4-chloro-6-methoxy-pyrimidin-2-yl)oxy]-3-methoxy-phthalide, 7-[(4,6-dimethoxy-pyrimidin-2-yl)oxy]-3-hydroxy-phthalide, 3-cyanomethoxy-7-[(4,6-dimethoxy-pyrimidin-2-yl)oxy]-phthalide, 7-[(4,6-dimethoxy-pyrimidin-2-yl)oxy]-3-(methoxycarbonyl-methoxy)-phthalide, 3-ethoxycarbonylmethyl-7-[(4,6-dimethoxy-pyrimidin-2-yl)oxy]-phthalide, 7-[(4,6-dimethoxy-pyrimidin-2-yl)oxy]-3-methyl-2-benzothiophen-1(3H)-one and 7-[(4,6-dimethoxy-pyrimidin-2-yl)oxy]-3-methyl-isobenzofuran-1(3H)-thione, and formulation adjuvants.

20. A method of controlling weeds and of regulating plant growth which comprises treating the crop to be protected against weeds and/or the weeds and the plants with an effective amount of a compound according to claim 1.

21. A method of controlling weeds which comprises treating the crop to be protected against weeds and/or the weeds with an effective amount of a compound according to claim 18.

* * * * *